United States Patent
Rubin et al.

(10) Patent No.: US 11,859,211 B2
(45) Date of Patent: Jan. 2, 2024

(54) SATELLITE CELLS AND COMPOSITIONS AND METHODS FOR PRODUCING THE SAME

(71) Applicant: President and Fellows of Harvard College, Cambridge, MA (US)

(72) Inventors: Lee L. Rubin, Cambridge, MA (US); Feodor D. Price, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 17/993,690

(22) Filed: Nov. 23, 2022

(65) Prior Publication Data

US 2023/0098750 A1   Mar. 30, 2023

Related U.S. Application Data

(60) Division of application No. 16/297,548, filed on Mar. 8, 2019, now Pat. No. 11,512,291, which is a continuation of application No. PCT/US2018/034458, filed on May 24, 2018.

(60) Provisional application No. 62/510,617, filed on May 24, 2017.

(51) Int. Cl.
   *A61K 35/12*   (2015.01)
   *A61K 35/34*   (2015.01)
   *C12N 5/077*   (2010.01)

(52) U.S. Cl.
   CPC ............ *C12N 5/0659* (2013.01); *A61K 35/12* (2013.01); *A61K 35/34* (2013.01); *C12N 5/0658* (2013.01); *C12N 2506/1323* (2013.01); *C12N 2513/00* (2013.01); *C12N 2527/00* (2013.01)

(58) Field of Classification Search
   CPC ................ C12N 5/0659; C12N 5/0658; C12N 2506/1323; C12N 2513/00; C12N 2527/00; A61K 35/12; A61K 35/34
   See application file for complete search history.

(56) References Cited

U.S. PATENT DOCUMENTS

| | | | |
|---|---|---|---|
| 11,512,291 | B2 | 11/2022 | Rubin et al. |
| 2005/0175978 | A1 | 8/2005 | Ramasubramanian |
| 2007/0190056 | A1 | 8/2007 | Kambadur et al. |
| 2009/0074730 | A1 | 3/2009 | Rudnicki et al. |
| 2011/0250691 | A1 | 10/2011 | Parent et al. |
| 2013/0004464 | A1 | 1/2013 | Nadal-Ginard |
| 2014/0193903 | A1 | 7/2014 | Oh et al. |
| 2015/0111822 | A1 | 4/2015 | Rudnicki et al. |
| 2015/0166961 | A1 | 6/2015 | Parker et al. |
| 2019/0203180 | A1 | 7/2019 | Rubin et al. |

FOREIGN PATENT DOCUMENTS

| | | |
|---|---|---|
| JP | 2012524727 A | 10/2012 |
| WO | 2010/124365 A1 | 11/2010 |
| WO | 2018/218061 A1 | 11/2018 |

OTHER PUBLICATIONS

Asakura A. et al., "Increased survival of muscle stem cells lacking the MyoD gene after transplantation into regenerating skeletal muscle", PNAS, Oct. 16, 2007, vol. 104, No. 42, p. 16552-16557. (Year: 2007).*
Zammit P.S. et al., "Muscle satellite cells adopt divergent fates: a mechanism for self-renewal?", The Journal of Cell Biology, vol. 166, No. 3 (Aug. 2, 2004), pp. 347-357. (Year: 2004).*
Ding C.—A Ph.D. Thesis entitled—"The influence of Notch over-stimulation on muscle stem cell quiescence versus proliferation, and on muscle regeneration", submitted in 2015 to The Department of Biology, Chemistry and Pharmacy, Freie Universitat, Berlin., total pp. 1-128. (Year: 2015).*
Abou-Khalil, et al., "Human and Murine Skeletal Muscle Reserve Cells," Methods in Molecular Biology, 1035:165-177, (2013).
Asakura, et al., "Increased Survival of Muscle Stem Cells Lacking the MyoD Gene After Transplantation Into Regenerating Skeletal Muscle," PNAS, 104(42):16552-16557, (Oct. 16, 2007).
Bentzinger, et al., "Fibronectin Regulates Wnt7a Signaling and Satellite Cell Expansion," Cell Stem Cell, 12:75-87, (Jan. 3, 2013).
Conboy, et al., "The Regulation of Notch Signaling Controls Satellite Cell Activation and Cell Fate Determination in Postnatal Myogenesis," Developmental Cell, 3(3):397-409, (Sep. 1, 2002).
Cornelison, et al., "Syndecan-3 and Syndecan-4 Specifically Mark Skeletal Muscle Satellite Cells and Are Implicated in Satellite Cell Maintenance and Muscle Regeneration," Developmental Biology, 239:79-94, (2001).
DeMicheli, et al., "Single-Cell Analysis of the Muscle Stem Cell Hierarchy Identifies Heterotypic Communication Signals Involved in Skeletal Muscle Regernetaion," Cell Reports, 30:3583-3595, (Mar. 10, 2020).
Ding, et al., "The Influence of Notch Over-Stimulation on Muscle Stem Cell Quiescence Versus Proliferation, and on Muscle Regeneration," Thesis submitted in 2015 to The Department of Biology, Chemistry and Pharmacy, Freie Univeritat, Berlin, pp. 1-128, (2015).
Fukuda, et al., "Molecular Signature of Quiescent Satellite Cells in Adult Skeletal Muscle," Stem Cells, 25:2448-2459, (2007).
International Search Report from PCT/US2018/034458, dated Oct. 24, 2018.
Kuang, et al., "Asymmetric Self-Renewal and Commitment of Satellite Stem Cells in Muscle," Cell, 129(5):999-1010, (Jun. 1, 2007).
Laumonier, et al., "Human Myogenic Reserve Cells are Quiescent Stem Cells that Contribute to Muscle Regeneration After Intramuscular Transplantation in Immunodeficient Mice," Scientific Reports, 7(3462):1-12, (Jun. 14, 2017).
Liu, et al., "Dedifferentiation of Primary Murine Myoblasts Induced by Ectopic Expression of Msx1," Molecular Therapy, 9:S145-S146, (May 1, 2004).

(Continued)

*Primary Examiner* — Satyendra K Singh
(74) *Attorney, Agent, or Firm* — Morse, Barnes-Brown & Pendleton, P.C.; Lisa M. Warren, Esq.; Erin E. Bryan, Esq.

(57) ABSTRACT

Disclosed herein are methods for generating satellite cells and compositions including satellite cells.

30 Claims, 22 Drawing Sheets

(56) References Cited

OTHER PUBLICATIONS

Machado, et al., "In Situ Fixation Redefines Quiescence and Early Activation of Skeletal Muscle Stem Cells," Cell Reports, 21:1982-1993, (Nov. 14, 2017).
Parmar, et al., "Tips to Manipulate Myogenesis: Retention of Myoblast Differentiation Capacity Using Microsphere Culture," European Cells and Materials, 30:41-50, (Jul. 27, 2015).
Rodgers, et al., "HGFA is an Injury-Regulated Systemic Factor that Induces the Transition of Stem Cells into GAlert," Cell Rep., 19(3):479-486, (Apr. 18, 2017).
Rodgers, et al., "mTORC1 Controls the Adaptive Transition of Quiescent Stem Cells from G0 to GAlert," Nature, 510:393-407, (Jun. 19, 2014).
Sakai, et al., "Notch Ligands Regulate the Muscle Stem-Like State ex vivo But Are Not Sufficient for Retaining Regenerative Capacity," PLOS One, pp. 1-18, (May 12, 2017).
Vial, et al., "Skeletal Muscle Cells Express the Profibrotic Cytokine Connective Tissue Growth Factor (CTGF/CCN2), Which Induces Their Dedifferentiation," Journal of Cellular Physiology, 215(2):410-421, (May 1, 2008).
Westerman, et al. "Myospheres are Composed of Two Cell Types: One that is Myogenic and a Second That is Mesenchymal," PLOS One, pp. 1-18, (Feb. 23, 2015).
Zammit, et al., "Muscle Satellite Cells Adopt Divergent Fates: A Mechanism for Self-Renewal?" The Journal of Cell Biology, 166(3):347-357, (Aug. 2, 2004).
Zhang, et al., "Islr Regulates Canonical Wnt Signaling-Mediated Skeletal Muscle Regeneration by Stabilizing Dishevelled-2 and Preventing Autophagy," Nat. Commun, 9:1-32, (Dec. 3, 2018).

* cited by examiner

FIG. 3C
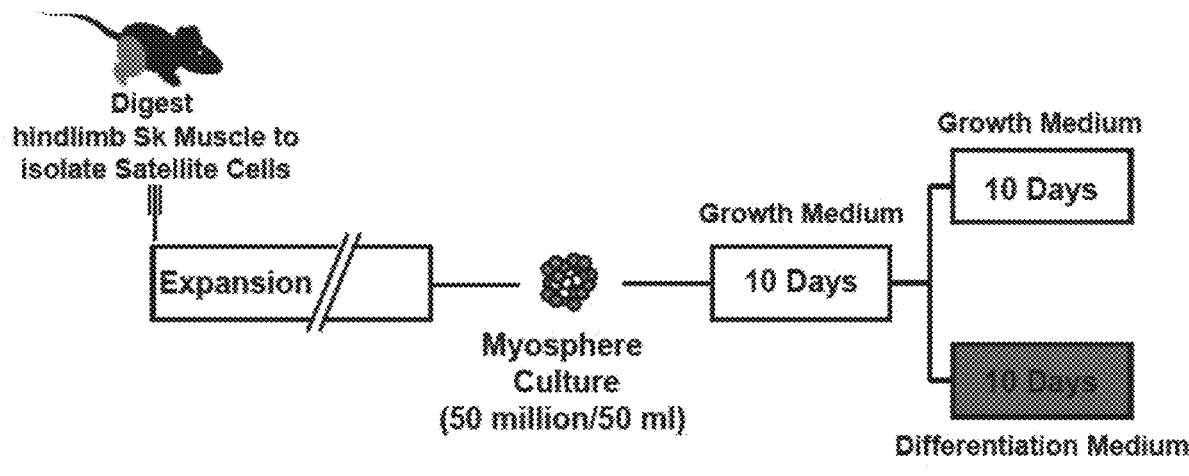
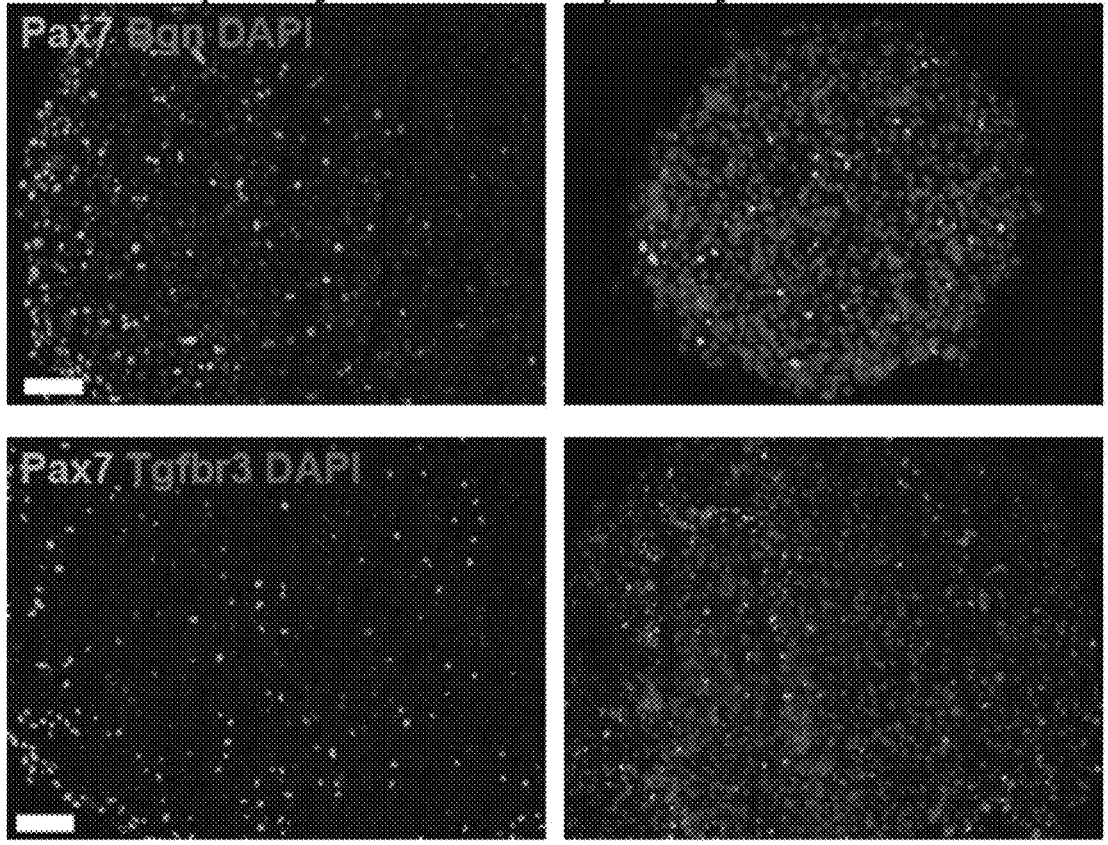
FIG. 3D

| UP ALL | | |
|---|---|---|
| Dcn | P2ry14 | Nav1 |
| Dpt | Pmp22 | Lamc1 |
| Heyl | Igf1 | Atp2b4 |
| Nr4a1 | S1pr3 | Tagln |
| Col4a1 | Klf9 | Mkl2 |
| Pax7 | Col6a1 | Col4a2 |
| Tgfbr3 | Txnip | Htra3 |
| Fos | Glul | Fxyd1 |
| Egr1 | Col6a2 | Ogn |
| Dag1 | Ncald | Tgfb3 |
| Apoe | Cc2d2a | Tcp11l2 |
| Spry1 | Gpm6b | Spats2l |
| Kat2b | Timp3 | Capn6 |
| Cav1 | Prkcdbp | Fgfr1 |
| Cd82 | Nfia | Mt2 |
| Igfbp4 | Gpr124 | Cdkn2c |
| Thbs2 | Psmb11 | Tln2 |
| Igfbp7 | Ccdc80 | Ndrg2 |
| Serping1 | Malat1 | Bhlhe40 |
| Fosb | Zfp36l1 | Fstl1 |
| Zfp36 | Gsn | Tcf4 |
| Nrep | Sdpr | Igsf3 |
| Sepp1 | Slc16a2 | Tmem123 |
| Junb | Olfml3 | Col3a1 |
| Ier2 | 1810026B05Rik | Emp2 |
| Col15a1 | Adamts1 | Itm2a |
| Adh1 | Olfml2b | Xbp1 |
| Cp | Gng11 | Crip1 |
| Ramp2 | Cd200 | Sparc |
| Sparcl1 | Fcgrt | Cd9 |

FIG. 8A

| DOWN ALL | | |
|---|---|---|
| Tspan9 | Ankrd1 | Tmem55a |
| Sema3e | Hes6 | Prdx6 |
| Hspd1 | Cox6b2 | Sox11 |
| Tipin | Gm15772 | Cited2 |
| Rasa1 | S100a6 | Ddx39 |
| Sct | Col18a1 | Slc44a2 |
| Mdm2 | Steap2 | Bax |
| Csf1 | Smyd4 | Gal |
| Mstn | Tmem171 | Rbmxl1 |
| Alox5 | Cttn | Mak16 |
| Ckap2 | Car3 | Nap1l1 |
| Camk1g | Rrm2 | Dctpp1 |
| Mcpt8 | Asns | Nme1 |
| Ccng1 | Chrna1 | Ccnd1 |
| Tuba1c | Ugcg | Cks1b |
| Rps27l | Cdh2 | Myl9 |
| Hmga2 | Myod1 | Prrc2c |
| Ccnb1 | Tpm1 | Set |
| Itga6 | Pa2g4 | Hnrnpf |
| Nasp | Fabp5 | Ppp1r14b |
| Dynap | Mcm4 | Ran |
| Myof | Rrm1 | Tuba1b |
| Epha2 | Ftl1 | Rbm3 |
| Gtse1 | Aaas | Hsp90aa1 |
| Lce1g | Tmsb10 | Nme2 |
| Cd24a | Lrrn1 | Hspe1 |
| Lgals3 | Ddx21 | Snrpg |
| Steap1 | Odc1 | Npm1 |

FIG. 8B

| UP SkMO | | |
|---|---|---|
| Itgb5 | Thbd | Rnf167 |
| Sdc1 | Uba7 | H1f0 |
| Vcan | Agtr2 | Fn1 |
| Bgn | Cyp1b1 | Mmp14 |
| Igfbp5 | Tspan15 | Cpq |
| Col5a1 | Osr2 | Mrc2 |
| Zcchc24 | Fam129a | Ifngr1 |
| Lum | Plekha6 | St3gal5 |
| Postn | Mmp2 | Fbn1 |
| Sfrp4 | Arrdc3 | Sdc2 |
| Spon2 | Matn2 | Adcy7 |
| Col8a1 | Mab21l1 | Ckm |
| Wisp2 | Pvrl2 | Hexa |
| Adamts2 | Adamtsl4 | Capg |
| Colec12 | Cd248 | Klhl13 |
| Dnm3os | Gulp1 | Loxl1 |
| Plat | Mfap2 | Fdft1 |
| 2310010J17Rik | Idua | Ifi27l1 |
| Ctsa | Cspg4 | Rbp1 |
| Ank | Spock1 | Nr2f2 |
| Dkk2 | Mfap4 | Cst3 |
| Fap | Hexb | Pxdn |
| Mmp3 | Cilp | Ecm1 |
| Dmp1 | Pold4 | Mybpc1 |
| Col6a3 | Crebrf | Igf2r |
| Pdgfrb | Col14a1 | Serpinh1 |
| Col1a1 | Tmem42 | Mt1 |
| Mgp | Nedd9 | Lpar1 |
| Tmem100 | Rcn3 | Atraid |
| Ctsr | Sept8 | Scd2 |
| Nr2f1 | Pcolce | Dap |
| Cfh | Edil3 | Ppic |
| Pdgfra | Nupr1 | App |
| Dio2 | Phf17 | Lamp2 |
| Htra1 | Plin3 | Col5a2 |
| Dkk3 | Aebp1 | Gpc1 |
| Islr | Hmgcs1 | Hspa5 |
| Foxs1 | P4ha1 | Pmepa1 |
| Tgfb2 | Lama2 | Laptm4a |
| Tgm2 | Csrp2 | Lrp1 |

FIG. 8C

| DOWN SkMO |
|---|
| Reln |
| Msln |
| Sema6d |
| Itgb4 |
| Ldhb |
| Nop58 |
| Dkc1 |
| Rpl12 |
| Gchfr |
| Mgmt |
| Milr1 |
| Fnbp1l |
| Anxa3 |
| Tek |
| 2010204K13Rik |
| Selp |
| Efnb2 |
| Cirh1a |
| Fgf21 |
| Stmn2 |
| Gpatch4 |
| Peg3 |
| Snhg8 |
| Fbl |
| Ahcy |
| Ebna1bp2 |
| Nop56 |
| Pcna |

FIG. 8D

SATELLITE CELLS AND COMPOSITIONS AND METHODS FOR PRODUCING THE SAME

RELATED APPLICATIONS

This application is a divisional of U.S. application Ser. No. 16/297,548 (now U.S. Pat. No. 11,512,291), filed on Mar. 8, 2019, which is a continuation of International Application No. PCT/US2018/034458, filed on May 24, 2018, which claims the benefit of U.S. Provisional Application No. 62/510,617, filed on May 24, 2017. The entire teachings of the above applications are incorporated herein by reference. International Application No. PCT/US2018/034458 was published under Article 21(2) in English.

BACKGROUND OF THE INVENTION

Skeletal muscle has a remarkable capacity to regenerate. This regenerative capacity is attributed to the satellite cell—a skeletal muscle stem cell (Collins et al., 2005; Kuang et al, 2007; Mauro, 1961). In response to damage or in a state of disease, satellite cells exit quiescence, proliferate and give rise to a transit-amplifying population of progenitors called myoblasts (Yin et al., 2013). When cultured in vitro satellite cells become myoblasts and lose their capacity to re-populate the stem cell niche following transplant in vivo (Montarras et al., 2005). To date no evidence exists demonstrating that myoblasts cultured in vitro can dedifferentiate back into satellite cells.

SUMMARY OF THE INVENTION

There is a need for methods or protocols for the generation of satellite cells in sufficient quantities to be useful for cell therapy and screening, among other uses. 3D culture systems (e.g., skeletal muscle organoids) described herein create a suitable niche for myoblasts cultured in vitro to dedifferentiate into satellite cells. The creation of this niche allows myoblasts to return to quiescence, take on the transcriptional signature of the satellite cell, and begin expressing critical glycoproteins present only in the satellite cell niche.

In some aspects, the disclosure provides a non-naturally occurring (i.e., non-native) satellite cell.

In some embodiments, the non-naturally occurring satellite cell exhibits a morphology that resembles the morphology of an endogenous or naturally occurring satellite cell. In some embodiments, the non-naturally occurring satellite cell expresses Pax7 and/or Myf5, and in some embodiments this expression is at levels consistent with the expression level of the respective gene in an endogenous or naturally occurring satellite cell. In some embodiments, the non-naturally occurring cell exhibits a response to a muscle injury. For example, the non-naturally occurring satellite cell may initiate or drive muscle regeneration following transplantation. In some embodiments, the non-naturally occurring satellite cell expresses at least one quiescence-related gene. The quiescence-related gene may, for example, be selected from the group consisting of Spry1, Nm1, Nfia, Fos, and Dusp1. In some embodiments, the non-naturally occurring satellite cell expresses at least one Notch signaling pathway gene. The Notch signaling pathway gene may be selected from the group consisting of Notch1, Notch2, Notch3, HeyL, Hey2, and Hes. In some embodiments, the non-naturally occurring satellite cell expresses Pax7, Myf5, at least one quiescence related gene, and at least one Notch signaling pathway gene.

In some embodiments, the non-naturally occurring satellite cell expresses at least one, at least two, or at least three of the genes identified in FIG. 8A and FIG. 8C herein. In some embodiments, the non-naturally occurring satellite cell expresses at least one, at least two, or at least three genes identified in FIG. 8C herein. The non-naturally occurring satellite cell does not express MyoD (a gene whose expression is associated with myoblasts).

In some embodiments, the non-naturally occurring satellite cell is dedifferentiated in vitro from a myoblast. The non-naturally occurring satellite cell may be derived from a dedifferentiated myoblast. The non-naturally occurring satellite cell may be human. In some embodiments, the non-naturally occurring satellite cell is not genetically modified, while in other embodiments it can be genetically modified. For example, the non-naturally occurring satellite cells may be modified to express, or express at increased levels, a protein of interest (e.g., insulin) which may be beneficial to a recipient of the cell(s). The non-naturally occurring satellite cell may have the capacity to repopulate the satellite cell niche and/or may be expandable in culture.

In some aspects, the disclosure provides a cell line comprising a non-naturally occurring satellite cell as described herein.

In some aspects, the disclosure provides a composition including a non-naturally occurring satellite cell, wherein the non-naturally occurring satellite cell is derived from a dedifferentiated myoblast; the non-naturally occurring satellite cell is expandable in culture; the non-naturally occurring satellite cell has capacity to repopulate the satellite cell niche; and the non-naturally occurring satellite cell drives muscle regeneration following transplantation.

In some aspects, the work described herein provides a method of generating a non-naturally occurring satellite cell from a population of myoblasts, the method comprising contacting a population of cells comprising myoblasts in spin culture with at least one medium for a time sufficient to induce the dedifferentiation of at least one myoblast in the spin culture into a non-naturally occurring satellite cell. In some embodiments, the at least one medium is a myoblast medium, a spin medium, and/or a differentiation medium.

In some aspects, the disclosure provides a method of generating a non-naturally occurring satellite cell from a population of myoblasts, the method comprising contacting a population of cells comprising myoblasts with a myoblast medium to form an expanded myoblast population; contacting an expanded myoblast population in spin culture with a spin medium to form at least one skeletal muscle organoid comprising differentiated and proliferative cells; and contacting the at least one skeletal muscle organoid in spin culture with a differentiation medium to induce the dedifferentiation of at least one proliferative cell of the skeletal muscle organoid into a non-naturally occurring satellite cell.

In some embodiments, the population of cells is maintained in a suspension culture of spin medium for a period of time sufficient to induce the in vitro maturation of at least one of the myoblasts (typically at least several) in the population of cells into at least one skeletal muscle organoid comprising differentiated and proliferative cells. In some embodiments, the period of time comprises at least 10 days, between 10 days and 30 days, or between 10 and 20 days. In some embodiments the period of time is 20 days.

In some embodiments, the at least one skeletal muscle organoid is maintained in a suspension culture for a period of time sufficient to induce the in vitro maturation of at least one of the proliferative cells of the skeletal muscle organoid into at least one non-naturally occurring satellite cell. In some embodiments, the period of time comprises at least 10 days, between 10 days and 30 days, or between 10 and 20 days; in some embodiments the period of time is 10 days. In some embodiments, at least 1% of the myoblasts in the population of cells are induced to dedifferentiate into non-naturally occurring satellite cells. The non-naturally occurring satellite cell described herein may thus be derived from a dedifferentiated myoblast.

In some embodiments, the generation of non-naturally occurring satellite cells in vitro is scalable. The non-naturally occurring satellite cell may be expandable in culture. In some embodiments, the non-naturally occurring satellite cell has capacity to repopulate the satellite cell niche.

In some aspects, the disclosure provides an isolated population of non-naturally occurring satellite cells produced according to the methods described herein.

In some aspects, the disclosure provides a microcapsule comprising the isolated population of non-naturally occurring satellite cells described herein encapsulated therein.

In some aspects, the disclosure provides a composition comprising a population of non-naturally occurring satellite cells produced according to the methods described herein.

In some aspects, the disclosure provides an assay to identify one or more candidate agents which promote the dedifferentiation of at least one myoblast into at least one non-naturally occurring satellite cell.

In some aspects, the disclosure provides a method for treatment of a subject in need thereof, the method comprising administering to a subject a composition comprising a non-naturally occurring satellite cell, e.g., an isolated population of non-naturally occurring satellite cells produced according to the methods described herein. In some embodiments, the satellite cells are encapsulated in a microcapsule. The non-naturally occurring satellite cells may be produced from a population of myoblasts obtained from the same subject to which the non-naturally occurring satellite cells are administered. In some embodiments, the subject has, or has an increased risk of developing, a muscle degenerative disorder, muscle trauma, or age-related muscle weakness (e.g., sarcopenia).

In some aspects, the disclosure provides the use of a population of non-naturally occurring satellite cells, e.g., produced by the methods described herein, for administering to a subject in need thereof. The isolated population of non-naturally occurring satellite cells may be administered to the subject encapsulated in microcapsules. In some embodiments, the subject has, or has an increased risk of developing, a muscle degenerative disorder, muscle trauma, or age related muscle weakness (e.g., sarcopenia).

The practice of the present invention will typically employ, unless otherwise indicated, conventional techniques of cell biology, cell culture, molecular biology, transgenic biology, microbiology, recombinant nucleic acid (e.g., DNA) technology, immunology, and RNA interference (RNAi) which are within the skill of the art. Non-limiting descriptions of certain of these techniques are found in the following publications: Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, 3rd ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988; Freshney, R. I., "Culture of Animal Cells, A Manual of Basic Technique", 5th ed., John Wiley & Sons, Hoboken, N J, 2005. Non-limiting information regarding therapeutic agents and human diseases is found in Goodman and Gilman's The Pharmacological Basis of Therapeutics, 11th Ed., McGraw Hill, 2005, Katzung, B. (ed.) Basic and Clinical Pharmacology, McGraw-Hill/Appleton & Lange; 10th ed. (2006) or 11th edition (July 2009). Non-limiting information regarding genes and genetic disorders is found in McKusick, V. A.: Mendelian Inheritance in Man. A Catalog of Human Genes and Genetic Disorders. Baltimore: Johns Hopkins University Press, 1998 (12th edition) or the more recent online database: Online Mendelian Inheritance in Man, OMIM™. McKusick-Nathans Institute of Genetic Medicine, Johns Hopkins University (Baltimore, MD) and National Center for Biotechnology Information, National Library of Medicine (Bethesda, MD), as of May 1, 2010, World Wide Web URL: ncbi.nlm.nih.gov/omim/and in Online Mendelian Inheritance in Animals (OMIA), a database of genes, inherited disorders and traits in animal species (other than human and mouse), at omia.angis.org.au/contact.shtml. All patents, patent applications, and other publications (e.g., scientific articles, books, websites, and databases) mentioned herein are incorporated by reference in their entirety. In case of a conflict between the specification and any of the incorporated references, the specification (including any amendments thereof, which may be based on an incorporated reference), shall control. Standard art-accepted meanings of terms are used herein unless indicated otherwise. Standard abbreviations for various terms are used herein.

BRIEF DESCRIPTION OF THE DRAWINGS

FIG. 1A depicts a schematic illustration outlining the isolation of myoblasts, as well as the expansion and culture in spin flasks to form three-dimensional skeletal muscle organoids. FIG. 1B shows murine three-dimensional skeletal muscle organoids at 10, 20, and 30 days post seeding into spin flasks. Immunofluorescent imaging with antibodies against Pax7 (green) and MyHC (red). Nuclei are counterstained with Hoechst. Scale bar denotes 100 μm. FIG. 1C shows human three-dimensional skeletal muscle organoids at 10 days post seeding into spheroid plates. Skeletal muscle organoids were transferred from spheroid plates at Day 2 into low adherence 10 cm plates for an additional 8 days of culture on an orbital shaker. FIG. 1D shows human three-dimensional skeletal muscle organoids at 10 days post seeding into spheroid plates. Immunofluorescent imaging with antibodies against Pax7 (green) and MyHC (red). Nuclei counterstained with Hoechst. Scale bar denotes 100 μm.

FIG. 2A provides a heat map depicting gene profile for satellite cells and cultured myoblasts. Red denotes genes that are upregulated while blue denotes genes that are downregulated between myoblasts and satellite cells. FIG. 2B shows qPCR validation from skeletal muscle organoid derived nGFP+ cells 30 days following culture in 3D. Experiments conducted in biological triplicate (n=3) using distinct myoblast lines derived from an individual Pax7nGFP mouse. Results are displayed as a log fold change relative to proliferating myoblasts.

FIGS. 3A-3D demonstrate skeletal muscle organoid derived satellite-like cells express proteoglycans unique to the satellite cell niche. FIG. 3A provides a heat map depicting a subset of satellite cell specific proteoglycan genes relative to their expression on cultured myoblasts Red denotes genes that are upregulated while blue denotes genes that are downregulated between myoblasts and satellite cells. FIG. 3B shows qPCR validation of proteoglycan genes from skeletal muscle organoid derived nGFP+ cells 30 days following culture in 3D. Experiments conducted in biological triplicate (n=3) using distinct myoblast lines derived from an individual Pax7nGFP mouse. Results are displayed as a log fold change relative to proliferating myoblasts. FIG. 3C provides a schematic of skeletal muscle organoid culture and differentiation to detect proteoglycans. FIG. 3D shows cryosectioned skeletal muscle organoids at day 20 or at day 10 differentiation. Immunofluorescent imaging with antibodies against Pax7 (green) and either Bgn (red-top) or Tgfbr3 (red-bottom). Nuclei counterstained with Hoechst. Scale bar denotes 100 μm.

FIG. 4A provides a schematic outlining the formation of skeletal muscle organoid (SkMO) cells. SkMO cells generally encompass SkMO 30D growth cells and SkMO 30D Diff cells. SkMO 30D growth cells are skeletal muscle organoid cells grown in spin culture medium for 30 days. SkMO 30D Diff cells are skeletal muscle organoid cells grown in spin culture medium for 20 days and differentiation medium for 10 days (also referred to herein as non-naturally occurring satellite cells). FIG. 4B shows SkMO 30D growth cells and SkMO 30D Diff cells. FIG. 4C shows that SkMO cells express Pax7, a key transcription factor for endogenous satellite cells. The transcriptional profile of the SkMOs is examined by RNAseq and their ability to cluster in state space is assessed using a multi-dimensional scaling plot as shown in FIG. 4D. The SkMO GFP+ cells (green and blue) approximate the endogenous satellite cells (red) in terms of their transcriptional signature. The SkMO D30 Growth cells (blue) are shown to be more proliferative than the SkMO D30 Diff cells (green), with the SkMO D30 Diff cells clustering closer to the endogenous satellite cells (red). FIG. 4E provides a global heat map and dendogram further confirming the data provided in FIG. 4D.

FIG. 5A provides results from an EdU incorporation assay (48 hour treatment) showing that myoblasts divide and incorporate EdU while endogenous satellite cells do not. SkMO derived cells are much more quiescent than myoblasts and are very similar (SkMO D30 Diff condition (red)) to endogenous satellite cells (purple) (FIG. 5B). FIG. 5C provides an in vitro assay that predicts satellite cell function. Satellite cells cultured as single cells in a suspension 96 well plate form clones, whereas myoblasts do not. This is akin to a classic clonal assay for adult stem cells. FIG. 5D shows the size of each clone derived from a given cell type. SkMO derived cells are more similar to endogenous satellite cells.

FIG. 6A provides a schematic illustrating the methods for the engraftment and repopulation of SkMO cells following transplant. FIGS. 6B-6C show a bioluminescent (BLI) signal originating from the SkMO treated leg, whereas with the myoblast treated leg the cells do not provide sufficient BLI signals (FIG. 6B). This was quantified over a 21 day time course (D2, D7, D14, and D21) and stats are included (FIG. 6C). FIG. 6D shows fibers from myoblasts and from SkMO D30 Diff cells that are donor derived. FIG. 6E provides quantification of the engraftment shown in FIG. 6D. FIG. 6F shows the repopulation of the satellite cell niche with cells following transplant with SkMO derived cells as compared to myoblasts.

FIG. 7B provides a schematic illustrating the methods for generating SkMO cells from human myoblasts and transplanting those cells. FIG. 7C provides BLI quantification for human myoblasts.

FIGS. 8A-8E identify genes upregulated and downregulated in endogenous satellite cells and SkMO cells. Multiplex RNA sequencing of the cells was performed to identify upregulated and downregulated genes in endogenous satellite cells and SkMO cells as compared to myoblasts. A number of genes upregulated (FIG. 8A) and downregulated (FIG. 8B) by >2 fold in endogenous satellite cells, SkMO D30 growth cells, and SkMO D30 Diff cells relative to myoblasts are identified. These genes may be used to broadly define an endogenous satellite cell. Genes involved in the canonical pathway are highlighted in green, and genes involved in the p53 pathway are highlighted in yellow. (Note* Pax7 and Tgfbr3 are identified in red because they were not identified by the multiplex RNA sequencing, but are known to be present in satellite and SkMO cells based on previously obtained data.) In addition, a number of genes upregulated (FIG. 8C) and downregulated (FIG. 8D) by >2 fold in SkMO D30 growth cells and SkMO D30 Diff cells relative to myoblasts, but that are not present in endogenous satellite cells, are identified. These genes may be used to distinguish a SkMO cell from endogenous satellite cells. Genes unique to SkMO cells, as compared to endogenous satellite cells, may be involved in various pathways including inhibition of Wnt signaling (highlighted in red) and/or proteasome activation (highlighted in purple). FIG. 8E provides a venn diagram demonstrating the overlap in genes that are upregulated and downregulated in endogenous satellite cells, SkMO D30 growth cells and SkMO D30 Diff cells. The pathways (Notch activation, Wnt inhibition, proteasome activation) that are involved are additionally identified.

DETAILED DESCRIPTION OF THE INVENTION

Figure 1A:
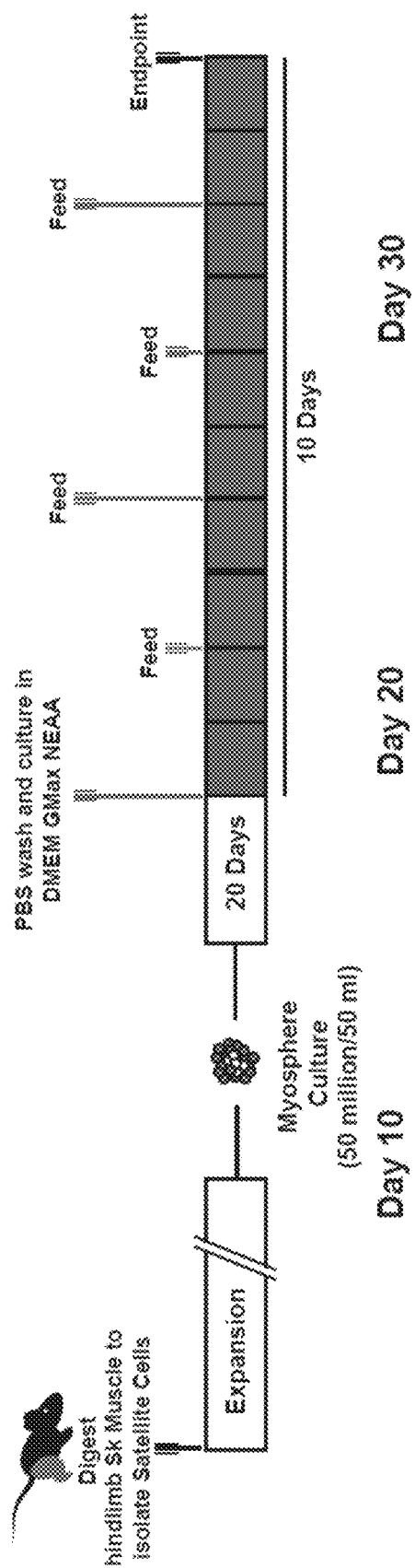
FIGS. 1A-1D depict culturing of three-dimensional skeletal muscle organoids.

Aspects of the disclosure relate to compositions, methods, kits, and agents for generating satellite cells (referred to herein as non-naturally occurring satellite cells or non-native satellite cells) from at least one myoblast, and satellite cells produced by those compositions, methods, kits, and agents for use in cell therapies, assays, and various methods of treatment.

The in vitro-produced satellite cells generated according to the methods described herein demonstrate many advantages; for example, they have the ability to repopulate the satellite cell niche and enhance muscle regeneration. In addition, the generated satellite cells may provide a new platform for cell therapy (e.g., transplantation into a subject in need of additional and/or functional satellite cells) and research.

Definitions

For convenience, certain terms employed herein, in the specification, examples and appended claims are collected here. Unless otherwise defined, all technical and scientific terms used herein have the same meaning as commonly understood by one of ordinary skill in the art to which this invention belongs.

As used herein, the term "somatic cell" refers to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell type: internal organs, skin, bones, blood, and connective tissue are all made up of somatic cells. In some embodiments the somatic cell is a "non-embryonic somatic cell," by which is meant a somatic cell that is not present in or obtained from an embryo and does not result from proliferation of such a cell in vitro. In some embodiments the somatic cell is an "adult somatic cell," by which is meant a cell that is present in or obtained from an organism other than an embryo or a fetus or results from proliferation of such a cell in vitro.

As used herein, the term "adult cell" refers to a cell found throughout the body after embryonic development.

The term "progenitor" or "precursor" cell are used interchangeably herein and refer to cells that have a cellular phenotype that is more primitive (i.e., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "phenotype" refers to one or a number of total biological characteristics that define the cell or organism under a particular set of environmental conditions and factors, regardless of the actual genotype.

The term "pluripotent" as used herein refers to a cell with the capacity to differentiate to more than one differentiated cell type, and preferably to differentiate to cell types characteristic of all three germ cell layers. Pluripotent cells are characterized primarily by their ability to differentiate to more than one cell type, preferably to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers. It should be noted that simply culturing such cells does not, on its own, render them pluripotent. Reprogrammed pluripotent cells (e.g., iPS cells as that term is defined herein) also have the characteristic of the capacity of extended passaging without loss of growth potential, relative to primary cell parents, which generally have capacity for only a limited number of divisions in culture.

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition, and it is essential as used in this document. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation" by persons of ordinary skill in the art. As used herein, the term "pluripotent stem cell" includes embryonic stem cells, induced pluripotent stem cells, placental stem cells, etc.

The terms "endogenous myosatellite cells" or "endogenous satellite cells" are used herein to refer to small mononuclear progenitor cells with virtually no cytoplasm found in mature muscle. They are found sandwiched between the basement membrane and sarcolemma (cell membrane) of individual muscle fibers, and can be difficult to distinguish from the sub-sarcolemmal nuclei of the fibers. Endogenous satellite cells are able to differentiate and fuse to augment existing muscle fibers and to form new fibers. These cells represent the oldest known adult stem cell niche, and are involved in the normal growth of muscle, as well as regeneration following injury or disease. In undamaged muscle, the majority of endogenous satellite cells are quiescent; they neither differentiate nor undergo cell division. In response to mechanical strain, endogenous satellite cells become activated. Activated endogenous satellite cells initially proliferate as skeletal myoblasts before undergoing myogenic differentiation. Endogenous satellite cells are distinguishable from the non-naturally occurring satellite cells of the invention by many of the characteristics described herein.

As used herein "satellite cell," "non-naturally occurring satellite cell," "non-native satellite cell," and "SkMO 30D Diff cell," all refer to a satellite cell that is generated via the dedifferentiation of a myoblast. Satellite cells may exhibit one or more features which may be shared with endogenous satellite cells, including, but not limited to, capacity to repopulate the satellite cell niche, ability to drive muscle regeneration, exhibit appropriate expression of gene markers, appropriate expression of glycoproteins, and expandability in culture. However non-naturally occurring satellite cells are not identical to and distinguishable from endogenous satellite cells as described herein, including distinction on the basis of gene expression.

As used herein, the term "proliferation" means growth and division of cells. In some embodiments, the term "proliferation" as used herein in reference to cells refers to a group of cells that can increase in number over a period of time.

As used herein, "inducing,", "enhancing," or "increasing" satellite cell proliferation means that satellite cells replicate at a faster rate and/or more frequently. In some embodiments of this and other aspects described herein, satellite cell proliferation is increased by at least 5%, 10%, 20%, 30%, 40%, 50%, 60%, 70%, 80%, 90%, 1-fold, 1.1-fold, 1.5-fold, 2-fold, 3-fold, 4-fold, 5-fold, 10-fold, 50-fold, 100-fold or more higher relative to an untreated control. The % or fold increase in satellite cell proliferation can be determined by measuring number of replicating satellite cells while in contact with a compound described herein relative to a control where the satellite cells are not in contact with the compound. Increase in proliferation can also be based on ratios of replicating cells to total number of cells in the respective treated and untreated control. In some embodiments, total number of cells in the treated and untreated controls is used to determine the proliferation. Satellite cell proliferation can be determined using the BrdU incorporation method described in U.S. Patent Publication No. 2009/0136481, content of which is incorporated herein by reference.

In the context of cell ontogeny, the adjective "differentiated", or "differentiating" is a relative term meaning a "differentiated cell" is a cell that has progressed further down the developmental pathway than the cell it is being compared with. Thus, stem cells can differentiate to lineage-restricted precursor cells (such as an ectodermal stem cell), which in turn can differentiate into other types of precursor cells further down the pathway (such as a neural ectodermal cell), and then to an end-stage differentiated cell, which plays a characteristic role in a certain tissue type, and may or may not retain the capacity to proliferate further.

The term "differentiated cell" is meant to include any primary cell that is not, in its native form, pluripotent as that term is defined herein. Stated another way, the term "differentiated cell" refers to a cell of a more specialized cell type derived from a cell of a less specialized cell type (e.g., a stem cell such as an induced pluripotent stem cell) in a cellular differentiation process.

In contrast, the adjective "dedifferentiated" or "dedifferentiating" is a relative term meaning a "dedifferentiated cell" is a cell that has reverted to a previous version of the cell on the developmental pathway. The term "dedifferentiated cell" is meant to include any cell that is a less specialized cell type derived from a more specialized cell type. For example, a myoblast may dedifferentiate to a satellite cell.

The term "cell culture medium" (also referred to herein as a "culture medium" or "medium") as referred to herein is a medium for culturing cells containing nutrients that maintain cell viability and support proliferation. The cell culture medium may contain any of the following in an appropriate combination: salt(s), buffer(s), amino acids, glucose or other sugar(s), antibiotics, serum or serum replacement, and other components such as peptide growth factors, etc. Cell culture media ordinarily used for particular cell types are known to those skilled in the art.

The term "nutrient medium" refers to a medium for culturing cells containing nutrients that promote proliferation. The nutrient medium may contain any of the following in an appropriate combination: isotonic saline, buffer, amino acids, antibiotics, serum or serum replacement, and exogenously added factors. A "conditioned medium" is prepared by culturing a first population of cells in a medium, and then harvesting the medium. The conditioned medium (along with anything secreted into the medium by the cells) may then be used to support the growth of a second population of cells.

Various mediums referred to herein include myoblast mediums, spin mediums, and differentiation mediums. The term "differentiation medium" refers to a medium for both differentiating and dedifferentiating a cell.

The term "agent" as used herein means any compound or substance such as, but not limited to, a small molecule, nucleic acid, polypeptide, peptide, drug, ion, etc. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc. In certain embodiments, agents are small molecule having a chemical moiety. For example, chemical moieties included unsubstituted or substituted alkyl, aromatic, or heterocyclyl moieties including macrolides, leptomycins and related natural products or analogues thereof. Compounds can be known to have a desired activity and/or property, or can be selected from a library of diverse compounds.

As used herein, the term "contacting" (i.e., contacting at least one embryoid body or a precursor thereof with a differentiation medium or agent) is intended to include incubating the differentiation medium and/or agent and the cell together in vitro (e.g., adding the differentiation medium or agent to cells in culture). In some embodiments, the term "contacting" is not intended to include the in vivo exposure of cells to the compounds as disclosed herein that may occur naturally in a subject (i.e., exposure that may occur as a result of a natural physiological process). The step of contacting at least one myoblast or a precursor thereof with a differentiation medium or agent as in the embodiments related to the production of satellite cells can be conducted in any suitable manner. For example, the cells may be treated in adherent culture, or in suspension culture. In some embodiments, the cells are treated in conditions that promote the formation of skeletal muscle organoids (also referred to herein as myospheres). The disclosure contemplates any conditions which promote the formation of skeletal muscle organoids. Examples of conditions that promote the formation of skeletal muscle organoids include, without limitation, suspension culture in low attachment tissue culture plates, spinner flasks, aggrewell plates. In some embodiments, the inventors have observed that skeletal muscle organoids have remained stable in media containing 20% serum (e.g., heat inactivated fetal bovine serum).

It is understood that the cells contacted with a differentiation medium and/or agent can also be simultaneously or subsequently contacted with another agent, such as other differentiation agents or environments to stabilize the cells, or to differentiate the cells further.

The term "exogenous" refers to a substance present in a cell or organism other than its native source. For example, the terms "exogenous nucleic acid" or "exogenous protein" refer to a nucleic acid or protein that has been introduced by a process involving the hand of man into a biological system such as a cell or organism in which it is not normally found or in which it is found in lower amounts. A substance will be considered exogenous if it is introduced into a cell or an ancestor of the cell that inherits the substance. In contrast, the term "endogenous" refers to a substance that is native to the biological system.

The term "expression" refers to the cellular processes involved in producing RNA and proteins and as appropriate, secreting proteins, including where applicable, but not limited to, for example, transcription, translation, folding, modification and processing. "Expression products" include RNA transcribed from a gene and polypeptides obtained by translation of mRNA transcribed from a gene.

The term "isolated" or "partially purified" as used herein refers, in the case of a nucleic acid or polypeptide, to a nucleic acid or polypeptide separated from at least one other component (e.g., nucleic acid or polypeptide) that is present with the nucleic acid or polypeptide as found in its natural source and/or that would be present with the nucleic acid or polypeptide when expressed by a cell, or secreted in the case of secreted polypeptides. A chemically synthesized nucleic acid or polypeptide or one synthesized using in vitro transcription/translation is considered "isolated".

The term "isolated cell" as used herein refers to a cell that has been removed from an organism in which it was originally found or a descendant of such a cell. Optionally the cell has been cultured in vitro, e.g., in the presence of other cells. Optionally the cell is later introduced into a second organism or re-introduced into the organism from which it (or the cell from which it is descended) was isolated.

The term "isolated population" with respect to an isolated population of cells as used herein refers to a population of cells that has been removed and separated from a mixed or heterogeneous population of cells. In some embodiments, an isolated population is a substantially pure population of cells as compared to the heterogeneous population from which the cells were isolated or enriched from.

The terms "enriching" or "enriched" are used interchangeably herein and mean that the yield (fraction) of cells of one type is increased by at least 10% over the fraction of cells of that type in the starting culture or preparation.

The term "modulate" is used consistently with its use in the art, i.e., meaning to cause or facilitate a qualitative or quantitative change, alteration, or modification in a process, pathway, or phenomenon of interest. Without limitation, such change may be an increase, decrease, or change in relative strength or activity of different components or branches of the process, pathway, or phenomenon. A "modulator" is an agent that causes or facilitates a qualitative or quantitative change, alteration, or modification in a process, pathway, or phenomenon of interest.

As used herein, the term "DNA" is defined as deoxyribonucleic acid.

A "marker" as used herein is used to describe the characteristics and/or phenotype of a cell. Markers can be used for selection of cells comprising characteristics of interests. Markers will vary with specific cells. Markers are characteristics, whether morphological, functional or biochemical (enzymatic) characteristics of the cell of a particular cell type, or molecules expressed by the cell type. Preferably, such markers are proteins, and more preferably, possess an epitope for antibodies or other binding molecules available in the art. However, a marker may consist of any molecule found in a cell including, but not limited to, proteins (peptides and polypeptides), lipids, polysaccharides, nucleic acids and steroids. Examples of morphological characteristics or traits include, but are not limited to, shape, size, and nuclear to cytoplasmic ratio. Examples of functional characteristics or traits include, but are not limited to, the ability to adhere to particular substrates, ability to incorporate or exclude particular dyes, ability to migrate under particular conditions, and the ability to differentiate or dedifferentiate along particular lineages. Markers may be detected by any method available to one of skill in the art. Markers can also be the absence of a morphological characteristic or absence of proteins, lipids etc. Markers can be a combination of a panel of unique characteristics of the presence and absence of polypeptides and other morphological characteristics.

The term "selectable marker" refers to a gene, RNA, or protein that when expressed, confers upon cells a selectable phenotype, such as resistance to a cytotoxic or cytostatic agent (e.g., antibiotic resistance), nutritional prototrophy, or expression of a particular protein that can be used as a basis to distinguish cells that express the protein from cells that do not. Proteins whose expression can be readily detected such as a fluorescent or luminescent protein or an enzyme that acts on a substrate to produce a colored, fluorescent, or luminescent substance ("detectable markers") constitute a subset of selectable markers. The presence of a selectable marker linked to expression control elements native to a gene that is normally expressed selectively or exclusively in pluripotent cells makes it possible to identify and select somatic cells that have been reprogrammed to a pluripotent state. A variety of selectable marker genes can be used, such as neomycin resistance gene (neo), puromycin resistance gene (puro), guanine phosphoribosyl transferase (gpt), dihydrofolate reductase (DHFR), adenosine deaminase (ada), puromycin-N-acetyltransferase (PAC), hygromycin resistance gene (hyg), multidrug resistance gene (mdr), thymidine kinase (TK), hypoxanthine-guanine phosphoribosyltransferase (HPRT), and hisD gene. Detectable markers include green fluorescent protein (GFP) blue, sapphire, yellow, red, orange, and cyan fluorescent proteins and variants of any of these. Luminescent proteins such as luciferase (e.g., firefly or *Renilla luciferase*) are also of use. As will be evident to one of skill in the art, the term "selectable marker" as used herein can refer to a gene or to an expression product of the gene, e.g., an encoded protein.

In some embodiments the selectable marker confers a proliferation and/or survival advantage on cells that express it relative to cells that do not express it or that express it at significantly lower levels. Such proliferation and/or survival advantage typically occurs when the cells are maintained under certain conditions, i.e., "selective conditions." To ensure an effective selection, a population of cells can be maintained under conditions and for a sufficient period of time such that cells that do not express the marker do not proliferate and/or do not survive and are eliminated from the population or their number is reduced to only a very small fraction of the population. The process of selecting cells that express a marker that confers a proliferation and/or survival advantage by maintaining a population of cells under selective conditions so as to largely or completely eliminate cells that do not express the marker is referred to herein as "positive selection", and the marker is said to be "useful for positive selection". Negative selection and markers useful for negative selection are also of interest in certain of the methods described herein. Expression of such markers confers a proliferation and/or survival disadvantage on cells that express the marker relative to cells that do not express the marker or express it at significantly lower levels (or, considered another way, cells that do not express the marker have a proliferation and/or survival advantage relative to cells that express the marker). Cells that express the marker can therefore be largely or completely eliminated from a population of cells when maintained in selective conditions for a sufficient period of time.

The terms "subject" and "individual" are used interchangeably herein, and refer to an animal, for example, a human from whom cells can be obtained and/or to whom treatment, including prophylactic treatment, with the cells as described herein, is provided. For treatment of those infections, conditions or disease states which are specific for a specific animal such as a human subject, the term subject refers to that specific animal. The "non-human animals" and "non-human mammals" as used interchangeably herein, includes mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like.

The terms "treat", "treating", "treatment", etc., as applied to an isolated cell, include subjecting the cell to any kind of process or condition or performing any kind of manipulation or procedure on the cell. As applied to a subject, the terms "treat", "treating", "treatment", etc. refer to providing medical or surgical attention, care, or management to an individual. The individual is usually ill or injured, or at increased risk of becoming ill relative to an average member of the population and in need of such attention, care, or management. It may include administering to a subject an effective amount of a composition so that the subject exhibits a reduction in at least one symptom of the disease or an improvement in the disease, for example, beneficial or desired clinical results. For purposes of this invention, beneficial or desired clinical results include, but are not limited to, alleviation of one or more symptoms, diminishment of extent of disease, stabilized (i.e., not worsening) state of disease, delay or slowing of disease progression, amelioration or palliation of the disease state, and remission (whether partial or total), whether detectable or undetectable. Treating can refer to prolonging survival as compared to expected survival if not receiving treatment. Thus, one of skill in the art realizes that a treatment may improve the disease condition, but may not be a complete cure for the disease. The term "treatment" includes prophylaxis. Those in need of treatment include those already diagnosed with a condition (e.g., muscle disorder or disease), as well as those likely to develop a condition due to genetic susceptibility or other factors.

The term "tissue" refers to a group or layer of specialized cells which together perform certain special functions. The term "tissue-specific" refers to a source of cells from a specific tissue.

The terms "decrease", "reduced", "reduction", "decrease" or "inhibit" are all used herein generally to mean a decrease by a statistically significant amount. However, for avoidance of doubt, "reduced", "reduction" or "decrease" or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90%, or up to and including a 100% decrease (i.e. absent level as compared to a reference sample), or any decrease between 10-100% as compared to a reference level.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90%, or up to and including a 100% increase or any increase between 10-100% as compared to a reference level, or at least about a 2-fold, or at least about a 3-fold, or at least about a 4-fold, or at least about a 5-fold, or at least about a 10-fold increase, or any increase between 2-fold and 10-fold or greater as compared to a reference level.

The term "statistically significant" or "significantly" refers to statistical significance and generally means a two standard deviation (2SD) below normal, or lower, concentration of the marker. The term refers to statistical evidence that there is a difference. It is defined as the probability of making a decision to reject the null hypothesis when the null hypothesis is actually true. The decision is often made using the p-value.

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Cloning and Cell Culture

Illustrative methods for molecular genetics and genetic engineering that may be used in the technology described herein may be found, for example, in current editions of Molecular Cloning: A Laboratory Manual, (Sambrook et al., Cold Spring Harbor); Gene Transfer Vectors for Mammalian Cells (Miller & Calos eds.); and Current Protocols in Molecular Biology (F. M. Ausubel et al. eds., Wiley & Sons). Cell biology, protein chemistry, and antibody techniques can be found, for example, in Current Protocols in Protein Science (J. E. Colligan et al. eds., Wiley & Sons); Current Protocols in Cell Biology (J. S. Bonifacino et al., Wiley & Sons) and Current protocols in Immunology (J. E. Colligan et al. eds., Wiley & Sons.). Illustrative reagents, cloning vectors, and kits for genetic manipulation may be commercially obtained, for example, from BioRad, Stratagene, Invitrogen, ClonTech, and Sigma-Aldrich Co.

Suitable cell culture methods may be found, for example, in the current edition of Culture of Animal Cells: A Manual of Basic Technique (R. I. Freshney ed., Wiley & Sons);

General Techniques of Cell Culture (M. A. Harrison & I. F. Rae, Cambridge Univ. Press), and Embryonic Stem Cells: Methods and Protocols (K. Turksen ed., Humana Press). Suitable tissue culture supplies and reagents are commercially available, for example, from Gibco/BRL, Nalgene-Nunc International, Sigma Chemical Co., and ICN Biomedicals.

Pluripotent stem cells can be propagated by one of ordinary skill in the art and continuously in culture, using culture conditions that promote proliferation without promoting differentiation. Exemplary serum-containing ES medium is made with 80% DMEM (such as Knock-Out DMEM, Gibco), 20% of either defined fetal bovine serum (FBS, Hyclone) or serum replacement (WO 98/30679), 1% non-essential amino acids, 1 mM L-glutamine, and 0.1 mM β-mercaptoethanol. Just before use, human bFGF is added to 4 ng/mL (WO 99/20741, Geron Corp.). Traditionally, ES cells are cultured on a layer of feeder cells, typically fibroblasts derived from embryonic or fetal tissue.

Alternatively, pluripotent SCs can be maintained in an undifferentiated state even without feeder cells. The environment for feeder-free cultures includes a suitable culture substrate, particularly an extracellular matrix such as MATRIGEL® (gelatinous protein mixture) or laminin. Typically, enzymatic digestion is halted before cells become completely dispersed (~5 min with collagenase IV). Clumps of ~10 to 2,000 cells are then plated directly onto the substrate without further dispersal.

Generating Satellite Cells

Aspects of the disclosure relate to generating satellite cells (e.g., skeletal muscle cells, and the like). Generally, the satellite cells produced according to the methods disclosed herein demonstrate several hallmarks of functional satellite cells, including, but not limited to, capacity to repopulate the satellite cell niche, drive muscle regeneration, demonstrate appropriate expression of gene markers, and are expandable in culture.

The satellite cells can be produced according to any suitable culturing protocol or series of culturing protocols to dedifferentiate a myoblast to a desired stage of dedifferentiation. In some embodiments, the satellite cells are produced by culturing at least one myoblast for a period of time and under conditions suitable for the at least one myoblast to dedifferentiate into the satellite cell. In some embodiments, the satellite cells is a substantially pure population of satellite cells.

In certain embodiments, myoblasts are cultured in a myoblast medium. The myoblasts may be cultured on microplates (e.g., collagen coated dishes) in the medium. In some embodiments, the myoblast medium includes a nutrient medium (e.g., Ham's F10), fetal bovine serum (e.g., 20% heat inactivated fetal bovine serum), fibroblast growth factor-basic, non-essential amino acids, and glutamax. The myoblasts may be cultured in the microplates for 1 to 30 days, 1 to 15 days, 1 to 10 days, 1 to 5 days, or about 4 days. In some aspects, the myoblasts are cultured on the microplates until reaching 50 to 100 confluence, 75 to 90 confluence, or about 80 confluence.

In some embodiments, the myoblasts are isolated from skeletal muscle of a subject. For example, the myoblasts may be isolated from the skeletal muscle of a human or a non-human animal, such as rats, mice, rabbits, sheep, cats, dogs, cows, pigs, and non-human primates. Alternatively, the myoblasts may be embryonic-derived muscle cells.

In certain embodiments, the myoblasts are cultured in the myoblast medium until reaching about 80 confluence and are then seeded into spinner flasks, spheroid plates, or the like. In some aspects, the spinner flasks are seeded at a density of about 500,000 cells/ml to about 1.5 million cells/ml, or about 750,000 cells/ml to about 1.25 million cells/ml, or about 1 million cells/ml. The myoblasts are cultured in the spinner flasks in a spin medium. In some embodiments, the spin medium includes basal medium (e.g., DMEM:F12), fetal bovine serum (e.g., 20% heat inactivated fetal bovine serum), fibroblast growth factor-basic, non-essential amino acids, and glutamax. The myoblasts may be cultured in the spinner flasks for at least 10 days, at least 20 days, at least 30 days, 10 to 30 days, 10 to 20 days, or in some aspects for 20 days. The resulting skeletal muscle organoids or myospheres are composed of a combination of Pax7+ and MyHC+ cells.

The myoblasts cultured in the spinner flasks in spin medium form three-dimensional spheres (e.g., myospheres or skeletal muscle organoids). In some aspects, the skeletal muscle organoids include differentiated skeletal muscle cells and proliferative myogenic cells. Upon formation of the skeletal muscle organoids, the medium may be changed to differentiation medium. In some aspects, the differentiation medium is a serum free medium. The differentiation medium may include a nutrient medium (e.g., DMEM), non-essential amino acids, and glutamax. In some aspects, the skeletal muscle organoids are cultured in differentiation medium for at least 1 day, at least 5 days, at least 10 days, 1 to 10 days, 1 to 30 days, 10 to 30 days, 10 to 20 days, or in some embodiments, for 10 days. During culture with the differentiation medium the proliferative myogenic cells present in the skeletal muscle organoids quiesce and return to a satellite cell state. The satellite cells may then be isolated from the medium.

In some embodiments, the satellite cells are expandable in culture. In some embodiments, the generated satellite cells are contacted with a compound to increase satellite cell proliferation. Method of inducing, enhancing or increasing satellite cell proliferation include contacting a satellite cell with a compound selected from the group consisting of kinase inhibitors, G protein coupled receptor (GPCR) modulators, epigenetic modifiers, histone deacetylases (HDAC) modulators, hedgehog signaling pathway modulators, neuropeptides, dopamine receptor modulators, serotonin receptor modulators, histamine receptor modulators, adenosine receptor agonists, ionophores, ion channel modulators, gamma-secretase modulators, corticosteroids, and any combinations thereof. Examples of proliferation enhancers include, but are not limited to, those described in PCT/US2017/016099, which is incorporated herein by reference.

Satellite Cells

In some embodiments, the disclosure provides functional satellite cells. In some embodiments, the methods of the invention allow for the generation of satellite cells that exhibit one or more features, including, but not limited to, capacity to repopulate the satellite cell niche, ability to drive muscle regeneration, exhibit appropriate expression of gene markers, appropriate expression of glycoproteins, and are expandable in culture.

In some embodiments, one can use any means common to one of ordinary skill in the art to confirm the presence of satellite cells produced by the dedifferentiation of myoblasts by exposure to at least one differentiation medium. In some embodiments, such satellite cells can be identified by selective gene expression markers. In some embodiments, the method can include detecting the positive expression (e.g. the presence) of a marker for satellite cells. In some embodiments, the marker can be detected using a reagent. A reagent for a marker can be, for example, an antibody against the marker or primers for a RT-PCR or PCR reaction, e.g., a semi-quantitative or quantitative RT-PCR or PCR reaction. Such markers can be used to evaluate whether a satellite cell has been produced. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The progression of at least one myoblast or precursor thereof to a satellite cell can be monitored by determining the expression of markers characteristic of satellite cells. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of satellite cells, as well as the lack of significant expression of markers characteristic of the myoblasts or precursors thereof is determined.

As described in connection with monitoring the production of satellite cells from a myoblast, qualitative or semi-quantitative techniques, such as blot transfer methods and immunocytochemistry, can be used to measure marker expression, using methods commonly known to persons of ordinary skill in the art. Alternatively, marker expression can be accurately quantitated through the use of technique such as quantitative-PCR by methods ordinarily known in the art.

In some embodiments, the generated satellite cells express one or more gene expression markers selected from core myogenic genes Pax7 and Myf5. Alternatively, or in addition, the generated satellite cells do not express the master transcription factor for skeletal muscle MyoD.

In some embodiments, the satellite cells can alternatively or in addition be characterized by expressing one or more markers selected from quiescence related genes Spry1, Nm1, Nfia, Fos, Dusp1, or any combination thereof. In some embodiments, the satellite cells of the skeletal muscle organoids culture can further be characterized by expressing one or more markers selected from the Notch signaling pathway Notch1, Notch2, Notch3, HeyL, Hey2, Hes, or any combination thereof. The satellite cells may express Pax7, Myf5, at least one quiescence related gene, and at least one Notch signaling pathway gene.

In some embodiments, the satellite cells express glycoproteins (e.g., glycoproteins typically present only in the satellite cell niche). The glycoprotein markers expressed by the satellite cells may include Bgn, TgfbrIII, Dag1, Dcn, and Gpc3.

In some embodiments, the satellite cells express at least one, at least two, at least three, at least four, at least five, at least six, at least seven, at least eight, at least nine, at least ten, at least fifteen, at least twenty, at least twenty-five, or at least thirty of the following genes: Dcn, Dpt, Hey1, Nr4a1, Col4a1, Pax7, Tgfbr3, Fos, Egr1, Dag1, Apoe, Spry1, Kat2b, Cav1, Cd82, Igfbp4, Thbs2, Igfbp7, Serping1, Fosb, Zfp36, Nrep, Sepp1, Junb, Ier2, Col15a1, Adh1, Cp, Ramp2, Sparcl1, P2ry14, Pmp22, Igf1, S1pr3, Klf9, Col6a1, Txnip, Glul, Col6a2, Ncald, Cc2d2a, Gpm6b, Timp3, Prkcdbp, Nfia, Gpr124, Psmb11, Ccdc80, Malat1, Zfp3611, Gsn, Sdpr, Slc16a2, Olfm13, 1810026B05Rik, Adamts1, Olfm12b, Gng11, Cd200, Fcgrt, Nav1, Lamc1, Atp2b4, Tagln, Mk12, Col4a2, Htra3, Fxyd1, Ogn, Tgfb3, Tcp1112, Spats21, Capn6, Fgfr1, Mt2, Cdkn2c, Tln2, Ndrg2, Bhlhe40, Fstl1, Tcf4, Igsf3, Tmem123, Col3a1, Emp2, Itm2a, Xbp1, Crip1, Sparc, Cd9, Itgb5, Sdc1, Vcan, Bgn, Igfbp5, Col5a1, Zcchc24, Lum, Postn, Sfrp4, Spon2, Col8a1, Wisp2, Adamts2, Colec12, Dnm3os, Plat, 2310010J17Rik, Ctsa, Ank, Dkk2, Fap, Mmp3, Dmpl, Col6a3, Pdgfrb, Col1a1, Mgp, Tmem100, Ctsc, Nr2f1, Cfh, Pdgfra, Dio2, Htra1, Dkk3, Islr, Foxs1, Tgfb2, Tgm2, Thbd, Uba7, Agtr2, Cyp1b1, Tspan15, Osr2, Fam129a, Plekha6, Mmp2, Arrdc3, Matn2, Mab2111, Pvr12, Adamts14, Cd248, Gulp1, Mfap2, Idua, Cspg4, Spock1, Mfap4, Hexb, Cilp, Pold4, Crebrf, Col14a1, Tmem42, Nedd9, Rcn3, Sept8, Pcolce, Edi13, Nupr1, Phf17, Plin3, Aebp1, Hmgcs1, P4ha1, Lama2, Csrp2, Rnf167, H1f0, Fn1, Mmp14, Cpq, Mrc2, Ifngr1, St3ga15, Fbn1, Sdc2, Adcy7, Ckm, Hexa, Capg, Klh113, Lox11, Fdft1, Ifi2711, Rbp1, Nr2f2, Cst3, Pxdn, Ecm1, Mybpc1, Igf2r, Serpinh1, Mt1, Lpar1, Atraid, Scd2, Dap, Ppic, App, Lamp2, Col5a2, Gpc1, Hspa5, Pmepa1, Laptm4a, and Lrp1. In some aspects, the expressed genes are upregulated at least 1.5 fold, at least 2 fold, at least 2.5 fold, or at least 3 fold, as compared to myoblasts.

In some embodiments, the satellite cells express at least one, at least two, at least three, at least four, at least five, at least six, at least seven, at least eight, at least nine, at least ten, at least fifteen, at least twenty, at least twenty-five, or at least thirty of the following genes: Dcn, Dpt, Hey1, Nr4a1, Col4a1, Pax7, Tgfbr3, Fos, Egr1, Dag1, Apoe, Spry1, Kat2b, Cav1, Cd82, Igfbp4, Thbs2, Igfbp7, Serping1, Fosb, Zfp36, Nrep, Sepp1, Junb, Ier2, Col15a1, Adh1, Cp, Ramp2, Sparcl1, P2ry14, Pmp22, Igf1, S1pr3, Klf9, Col6a1, Txnip, Glul, Col6a2, Ncald, Cc2d2a, Gpm6b, Timp3, Prkcdbp, Nfia, Gpr124, Psmb11, Ccdc80, Malat1, Zfp3611, Gsn, Sdpr, Slc16a2, Olfm13, 1810026B05Rik, Adamts1, Olfm12b, Gng11, Cd200, Fcgrt, Nav1, Lamc1, Atp2b4, Tagln, Mk12, Col4a2, Htra3, Fxyd1, Ogn, Tgfb3, Tcp1112, Spats21, Capn6, Fgfr1, Mt2, Cdkn2c, Tln2, Ndrg2, Bhlhe40, Fstl1, Tcf4, Igsf3, Tmem123, Col3a1, Emp2, Itm2a, Xbp1, Crip1, Sparc, and Cd9. In some aspects, the expressed genes are upregulated at least 1.5 fold, at least 2 fold, at least 2.5 fold, or at least 3 fold, as compared to myoblasts.

In some embodiments, the satellite cells express at least one, at least two, at least three, at least four, at least five, at least six, at least seven, at least eight, at least nine, at least ten, at least fifteen, at least twenty, at least twenty-five, or at least thirty of the following genes: Itgb5, Sdc1, Vcan, Bgn, Igfbp5, Col5a1, Zcchc24, Lum, Postn, Sfrp4, Spon2, Col8a1, Wisp2, Adamts2, Colec12, Dnm3os, Plat, 2310010J17Rik, Ctsa, Ank, Dkk2, Fap, Mmp3, Dmpl, Col6a3, Pdgfrb, Col1a1, Mgp, Tmem100, Ctsc, Nr2f1, Cfh, Pdgfra, Dio2, Htra1, Dkk3, Islr, Foxs1, Tgfb2, Tgm2, Thbd, Uba7, Agtr2, Cyp1b1, Tspan15, Osr2, Fam129a, Plekha6, Mmp2, Arrdc3, Matn2, Mab2111, Pvr12, Adamts14, Cd248, Gulp1, Mfap2, Idua, Cspg4, Spock1, Mfap4, Hexb, Cilp, Pold4, Crebrf, Col14a1, Tmem42, Nedd9, Rcn3, Sept8, Pcolce, Edi13, Nupr1, Phf17, Plin3, Aebp1, Hmgcs1, P4ha1, Lama2, Csrp2, Rnf167, H1f0, Fn1, Mmp14, Cpq, Mrc2, Ifngr1, St3ga15, Fbn1, Sdc2, Adcy7, Ckm, Hexa, Capg, Klh113, Lox11, Fdft1, Ifi2711, Rbp1, Nr2f2, Cst3, Pxdn, Ecm1, Mybpc1, Igf2r, Serpinh1, Mt1, Lpar1, Atraid, Scd2, Dap, Ppic, App, Lamp2, Col5a2, Gpc1, Hspa5, Pmepa1, Laptm4a, and Lrp1. In some aspects, the expressed genes are upregulated at least 1.5 fold, at least 2 fold, at least 2.5 fold, or at least 3 fold, as compared to myoblasts.

In some embodiments, the satellite cells express at least one of Pax7, Tgfbr3, Fos, Spry1, Cav1, and Cd82. The expressed genes may be upregulated by at least two fold as compared to myoblasts.

In some embodiments, the satellite cells express one or more genes involved in Wnt pathway inhibition. In some aspects, genes involved in Wnt pathway inhibition are selected from the group consisting of: Sfrp4, Wisp2, Dkk2, and Dkk3.

In some embodiments, the satellite cells express one or more genes involved in proteasome activation. In some aspects, genes involved in proteasome activation are selected from the group consisting of: Ctsa, Ctsc, Idua, Hexb, Hexa, Igf2r, Lamp2, and Laptm4a.

In some embodiments, the satellite cells downregulate expression of at least one, at least two, at least three, at least four, at least five, at least six, at least seven, at least eight, at least nine, at least ten, at least fifteen, at least twenty, at least twenty-five, or at least thirty of the following genes: Tspan9, Sema3e, Hspd1, Tipin, Rasa1, Sct, Mdm2, Csf1, Mstn, Alox5, Ckap2, Camk1g, Mcpt8, Ccng1, Tuba1c, Rps27l, Hmga2, Ccnb1, Itga6, Nasp, Dynap, Myof, Epha2, Gtse1, Lce1g, Cd24a, Lgals3, Steap1, Ankrd1, Hes6, Cox6b2, Gm15772, S100a6, Col18a1, Steap2, Smyd4, Tmem171, Cttn, Car3, Rrm2, Asns, Chrna1, Ugcg, Cdh2, Myod1, Tpm1, Pa2g4, Fabp5, Mcm4, Rrm1, Ftl1, Aaas, Tmsb10, Lrrn1, Ddx21, Odc1, Tmem55a, Prdx6, Sox11, Cited2, Ddx39, Slc44a2, Bax, Gal, Rbmx1l, Mak16, Nap1l1, Dctpp1, Nme1, Ccnd1, Cks1b, My19, Prrc2c, Set, Hnrnpf, Ppp1r14b, Ran, Tuba1b, Rbm3, Hsp90aa1, Nme2, Hspe1, Snrpg, Npm1, Reln, Msln, Sema6d, Itgb4, Ldhb, Nop58, Dkc1, Rpl12, Gchfr, Mgmt, Milr1, Fnbp11, Anxa3, Tek, 2010204K13Rik, Selp, Efnb2, Cirh1a, Fgf21, Stmn2, Gpatch4, Peg3, Snhg8, Fbl, Ahcy, Ebna1bp2, Nop56, and Pcna. In some aspects, expression is downregulated by at least 1.5 fold, at least 2 fold, at least 2.5 fold, or at least 3 fold, as compared to myoblasts.

In some embodiments, the satellite cells downregulate expression of at least one, at least two, at least three, at least four, at least five, at least six, at least seven, at least eight, at least nine, at least ten, at least fifteen, at least twenty, at least twenty-five, or at least thirty of the following genes: Tspan9, Sema3e, Hspd1, Tipin, Rasa1, Sct, Mdm2, Csf1, Mstn, Alox5, Ckap2, Camk1g, Mcpt8, Ccng1, Tuba1c, Rps27l, Hmga2, Ccnb1, Itga6, Nasp, Dynap, Myof, Epha2, Gtse1, Lce1g, Cd24a, Lgals3, Steap1, Ankrd1, Hes6, Cox6b2, Gm15772, S100a6, Col18a1, Steap2, Smyd4, Tmem171, Cttn, Car3, Rrm2, Asns, Chrna1, Ugcg, Cdh2, Myod1, Tpm1, Pa2g4, Fabp5, Mcm4, Rrm1, Ftl1, Aaas, Tmsb10, Lrrn1, Ddx21, Odc1, Tmem55a, Prdx6, Sox11, Cited2, Ddx39, Slc44a2, Bax, Gal, Rbmx1l, Mak16, Nap1l1, Dctpp1, Nme1, Ccnd1, Cks1b, My19, Prrc2c, Set, Hnrnpf, Ppp1r14b, Ran, Tuba1b, Rbm3, Hsp90aa1, Nme2, Hspe1, Snrpg, and Npm1. In some aspects, expression is downregulated by at least 1.5 fold, at least 2 fold, at least 2.5 fold, or at least 3 fold, as compared to myoblasts.

In some embodiments, the satellite cells downregulate expression of at least one, at least two, at least three, at least four, at least five, at least six, at least seven, at least eight, at least nine, at least ten, at least fifteen, at least twenty, or at least twenty-five of the following genes: Reln, Msln, Sema6d, Itgb4, Ldhb, Nop58, Dkc1, Rpl12, Gchfr, Mgmt, Milr1, Fnbp11, Anxa3, Tek, 2010204K13Rik, Selp, Efnb2, Cirh1a, Fgf21, Stmn2, Gpatch4, Peg3, Snhg8, Fbl, Ahcy, Ebna1bp2, Nop56, and Pcna. In some aspects, expression is downregulated by at least 1.5 fold, at least 2 fold, at least 2.5 fold, or at least 3 fold, as compared to myoblasts.

It is understood that the present invention is not limited to those markers listed as satellite cell markers herein, and the present invention also encompasses markers such as cell surface markers, antigens, and other gene products including ESTs, RNA (including microRNAs and antisense RNA), DNA (including genes and cDNAs), and portions thereof.

Markers characteristic of satellite cells include the expression of cell surface proteins or the encoding genes, the expression of intracellular proteins or the encoding genes, cell morphological characteristics, and the like. Those skilled in the art will recognize that known immunofluorescent, immunochemical, polymerase chain reaction, in situ hybridization, Northern blot analysis, chemical or radiochemical or biological methods can readily ascertain the presence or absence of satellite cell specific characteristics.

Aspects of the disclosure relate to isolated populations of satellite cells produced according to methods described herein. An isolated population of satellite cells can be obtained by dedifferentiating at least some myoblasts in a population into satellite cells.

Aspects of the disclosure involve microcapsules comprising isolated populations of cells described herein (e.g., satellite cells). Microcapsules are well known in the art. Suitable examples of microcapsules are described in the literature (e.g., Orive et al., "Application of cell encapsulation for controlled delivery of biological therapeutics", *Advanced Drug Delivery Reviews* (2013), dx.doi.org/10.1016/j.addr.2013.07.009; Hernandez et al., "Microcapsules and microcarriers for in situ cell delivery", *Advanced Drug Delivery Reviews* 2010; 62:711-730; Murua et al., "Cell microencapsulation technology: Towards clinical application", *Journal of Controlled Release* 2008; 132:76-83; and Zanin et al., "The development of encapsulated cell technologies as therapies for neurological and sensory diseases", *Journal of Controlled Release* 2012; 160:3-13). Microcapsules can be formulated in a variety of ways. Exemplary microcapsules comprise an alginate core surrounded by a polycation layer covered by an outer alginate membrane. The polycation membrane forms a semipermeable membrane, which imparts stability and biocompatibility. Examples of polycations include, without limitation, poly-L-lysine, poly-L-ornithine, chitosan, lactose modified chitosan, and photopolymerized biomaterials. In some embodiments, the alginate core is modified, for example, to produce a scaffold comprising an alginate core having covalently conjugated oligopeptides with an RGD sequence (arginine, glycine, aspartic acid). In some embodiments, the alginate core is modified, for example, to produce a covalently reinforced microcapsule having a chemoenzymatically engineered alginate of enhanced stability. In some embodiments, the alginate core is modified, for example, to produce membrane-mimetic films assembled by in-situ polymerization of acrylate functionalized phospholipids. In some embodiments, microcapsules are composed of enzymatically modified alginates using epimerases. In some embodiments, microcapsules comprise covalent links between adjacent layers of the microcapsule membrane. In some embodiment, the microcapsule comprises a subsieve-size capsule comprising alginate coupled with phenol moieties. In some embodiments, the microcapsule comprises a scaffold comprising alginate-agarose. In some embodiments, the satellite cell is modified with PEG before being encapsulated within alginate. In some embodiments, the isolated populations of cells, e.g., satellite cells are encapsulated in photoreactive liposomes and alginate. It should be appreciated that the alginate employed in the microcapsules can be replaced with other suitable biomaterials, including, without limitation, PEG, chitosan, PES hollow fibers, collagen, hyaluronic acid, dextran with RGD, EHD and PEGDA, PMBV and PVA, PGSAS, agarose, agarose with gelatin, PLGA, and multilayer embodiments of these.

Confirmation of the Presence and the Identification of Satellite Cells

One can use any means common to one of ordinary skill in the art to confirm the presence of a satellite cell, e.g. a non-naturally occurring satellite cell produced by the dedifferentiation of a myoblast as described herein.

In some embodiments, the presence of satellite cell markers, e.g. chemically induced satellite cells, can be done by detecting the presence or absence of one or more markers indicative of an endogenous satellite cell. In some embodiments, the method can include detecting the positive expression (e.g. the presence) of a marker for satellite cells. In some embodiments, the marker can be detected using a reagent, e.g., a reagent for the detection of Pax7 and Myf5. Additional markers to be detected include Notch signaling pathway markers Notch 1, Notch 2, Notch3, HeyL, Hey2 and Hes1, and quiescence related genes or markers Nm1, Nfia, Fos, Spry1, and Dusp1. Still other markers to be detected may be selected from the group consisting of: Dcn, Dpt, Hey1, Nr4a1, Col4a1, Pax7, Tgfbr3, Fos, Egr1, Dag1, Apoe, Spry1, Kat2b, Cav1, Cd82, Igfbp4, Thbs2, Igfbp7, Serping1, Fosb, Zfp36, Nrep, Sepp1, Junb, Ier2, Col15a1, Adh1, Cp, Ramp2, Sparcl1, P2ry14, Pmp22, Igf1, S1pr3, Klf9, Col6a1, Txnip, Glul, Col6a2, Ncald, Cc2d2a, Gpm6b, Timp3, Prkcdbp, Nfia, Gpr124, Psmb11, Ccdc80, Malat1, Zfp3611, Gsn, Sdpr, Slc16a2, Olfm13, 1810026B05Rik, Adamts1, Olfm12b, Gng11, Cd200, Fcgrt, Nav1, Lamc1, Atp2b4, Tagln, Mk12, Col4a2, Htra3, Fxyd1, Ogn, Tgfb3, Tcp1112, Spats21, Capn6, Fgfr1, Mt2, Cdkn2c, Tln2, Ndrg2, Bhlhe40, Fstl1, Tcf4, Igsf3, Tmem123, Col3a1, Emp2, Itm2a, Xbp1, Crip1, Sparc, Cd9, Itgb5, Sdc1, Vcan, Bgn, Igfbp5, Col5a1, Zcchc24, Lum, Postn, Sfrp4, Spon2, Col8a1, Wisp2, Adamts2, Colec12, Dnm3os, Plat, 2310010J17Rik, Ctsa, Ank, Dkk2, Fap, Mmp3, Dmpl, Col6a3, Pdgfrb, Col1a1, Mgp, Tmem100, Ctsc, Nr2f1, Cfh, Pdgfra, Dio2, Htra1, Dkk3, Islr, Foxs1, Tgfb2, Tgm2, Thbd, Uba7, Agtr2, Cyp1b1, Tspan15, Osr2, Fam129a, Plekha6, Mmp2, Arrdc3, Matn2, Mab2111, Pvr12, Adamts14, Cd248, Gulp1, Mfap2, Idua, Cspg4, Spock1, Mfap4, Hexb, Cilp, Pold4, Crebrf, Col14a1, Tmem42, Nedd9, Rcn3, Sept8, Pcolce, Edi13, Nupr1, Phf17, Plin3, Aebp1, Hmgcs1, P4ha1, Lama2, Csrp2, Rnf167, H1f0, Fn1, Mmp14, Cpq, Mrc2, Ifngr1, St3ga15, Fbn1, Sdc2, Adcy7, Ckm, Hexa, Capg, Klh113, Lox11, Fdft1, Ifi2711, Rbp1, Nr2f2, Cst3, Pxdn, Ecm1, Mybpc1, Igf2r, Serpinh1, Mt1, Lpar1, Atraid, Scd2, Dap, Ppic, App, Lamp2, Col5a2, Gpc1, Hspa5, Pmepa1, Laptm4a, and Lrp1.

A reagent for a marker can be, for example, an antibody against the marker or primers for a RT-PCR or PCR reaction, e.g., a semi-quantitative or quantitative RT-PCR or PCR reaction. Such markers can be used to evaluate whether a satellite cell has been produced. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

In some embodiments, the presence of satellite cell markers can be done by detecting the presence or absence of one or more markers indicative of a satellite cell. For example, a satellite cell may be identified from an endogenous satellite cell. In some embodiments, the method can include detecting the positive expression (e.g. the presence) of a marker for satellite cells. The marker may be selected from the group consisting of Itgb5, Sdc1, Vcan, Bgn, Igfbp5, Col5a1, Zcchc24, Lum, Postn, Sfrp4, Spon2, Col8a1, Wisp2, Adamts2, Colec12, Dnm3os, Plat, 2310010J17Rik, Ctsa, Ank, Dkk2, Fap, Mmp3, Dmpl, Col6a3, Pdgfrb, Col1a1, Mgp, Tmem100, Ctsc, Nr2f1, Cfh, Pdgfra, Dio2, Htra1, Dkk3, Islr, Foxs1, Tgfb2, Tgm2, Thbd, Uba7, Agtr2, Cyp1b1, Tspan15, Osr2, Fam129a, Plekha6, Mmp2, Arrdc3, Matn2, Mab2111, Pvr12, Adamts14, Cd248, Gulp1, Mfap2, Idua, Cspg4, Spock1, Mfap4, Hexb, Cilp, Pold4, Crebrf, Col14a1, Tmem42, Nedd9, Rcn3, Sept8, Pcolce, Edi13, Nupr1, Phf17, Plin3, Aebp1, Hmgcs1, P4ha1, Lama2, Csrp2, Rnf167, H1f0, Fn1, Mmp14, Cpq, Mrc2, Ifngr1, St3ga15, Fbn1, Sdc2, Adcy7, Ckm, Hexa, Capg, Klh113, Lox11, Fdft1, Ifi2711, Rbp1, Nr2f2, Cst3, Pxdn, Ecm1, Mybpc1, Igf2r, Serpinh1, Mt1, Lpar1, Atraid, Scd2, Dap, Ppic, App, Lamp2, Col5a2, Gpc1, Hspa5, Pmepa1, Laptm4a, and Lrp1.

The progression of at least one myoblast or precursor thereof to a satellite cell can be monitored by determining the expression of markers characteristic of satellite cells. In some processes, the expression of certain markers is determined by detecting the presence or absence of the marker. Alternatively, the expression of certain markers can be determined by measuring the level at which the marker is present in the cells of the cell culture or cell population. In certain processes, the expression of markers characteristic of satellite cells as well as the lack of significant expression of markers characteristic of the myoblasts or precursors thereof from which it was derived is determined.

As described in connection with monitoring the production of a satellite cell from a myoblast, qualitative or semi-quantitative techniques, such as blot transfer methods and immunocytochemistry, can be used to measure marker expression, using methods commonly known to persons of ordinary skill in the art. Alternatively, marker expression can be accurately quantitated through the use of technique such as quantitative-PCR by methods ordinarily known in the art. As such, techniques for measuring extracellular marker content, such as ELISA, may be utilized.

It is understood that the present invention is not limited to those markers listed as satellite cell markers herein, and the present invention also encompasses markers such as cell surface markers (e.g., CD56, EGFR, and β1-Integrin), antigens, and other gene products including ESTs, RNA (including microRNAs and antisense RNA), DNA (including genes and cDNAs), and portions thereof.

Enrichment, Isolation and Purification of a Satellite Cell

Another aspect of the present invention relates to the isolation of a population of satellite cells from a heterogeneous population of cells, such a mixed population of cells comprising satellite cells, myoblasts, differentiated skeletal muscle cells, and proliferative myogenic cells. A population of satellite cells produced by any of the above-described processes can be enriched, isolated and/or purified by using any cell surface marker present on the satellite cells which is not present on the myoblast or precursor thereof from which it was derived. Such cell surface markers are also referred to as an affinity tag which is specific for a satellite cell. Examples of affinity tags specific for satellite cells are antibodies, ligands or other binding agents that are specific to a marker molecule, such as a polypeptide, that is present on the cell surface of a satellite cells but which is not substantially present on other cell types (e.g. myoblasts). In some processes, an antibody which binds to a cell surface antigen on a satellite cell is used as an affinity tag for the enrichment, isolation or purification of chemically induced (e.g. by contacting with at least one differentiation medium as described herein) satellite cells produced by the methods described herein. Such antibodies are known and commercially available.

The skilled artisan will readily appreciate the processes for using antibodies for the enrichment, isolation and/or purification of satellite cells. For example, in some embodiments, the reagent, such as an antibody, is incubated with a cell population comprising satellite cells, wherein the cell population has been treated to reduce intercellular and substrate adhesion. The cell population is then washed, centrifuged and resuspended. In some embodiments, if the antibody is not already labeled with a label, the cell suspension is then incubated with a secondary antibody, such as an FITC-conjugated antibody that is capable of binding to the primary antibody. The satellite cells are then washed, centrifuged and resuspended in buffer. The satellite cell suspension is then analyzed and sorted using a fluorescence activated cell sorter (FACS). Antibody-bound, fluorescent reprogrammed cells are collected separately from non-bound, non-fluorescent cells, thereby resulting in the isolation of satellite cells from other cells present in the cell suspension, e.g. myoblasts, differentiated skeletal muscle cells or proliferative myogenic cells.

In another embodiment of the processes described herein, the isolated cell composition comprising satellite cells can be further purified by using an alternate affinity-based method or by additional rounds of sorting using the same or different markers that are specific for satellite cells. For example, in some embodiments, FACS sorting is used to first isolate a satellite cell which expresses Myf5, either alone or with the expression of Pax7, or alternatively with a satellite cell marker disclosed herein from cells that do not express one of those markers (e.g. negative cells) in the cell population. A second FAC sorting, e.g. sorting the positive cells again using FACS to isolate cells that are positive for a different marker than the first sort enriches the cell population for reprogrammed cells.

In an alternative embodiment, FACS sorting is used to separate cells by negatively sorting for a marker that is present on most myoblasts but is not present on satellite cells.

In some embodiments of the processes described herein, satellite cells are fluorescently labeled without the use of an antibody then isolated from non-labeled cells by using a fluorescence activated cell sorter (FACS). In such embodiments, a nucleic acid encoding GFP, YFP or another nucleic acid encoding an expressible fluorescent marker gene, such as the gene encoding luciferase, is used to label reprogrammed cells using the methods described above.

In addition to the procedures just described, chemically induced satellite cells may also be isolated by other techniques for cell isolation. Additionally, satellite cells may also be enriched or isolated by methods of serial subculture in growth conditions which promote the selective survival or selective expansion of the satellite cells. Such methods are known by persons of ordinary skill in the art.

In some embodiments, the isolated satellite cells are expandable in culture. In some embodiments, the isolated satellite cells are contacted with a compound to increase satellite cell proliferation. Method of inducing, enhancing or increasing satellite cell proliferation include contacting a satellite cell with a compound selected from the group consisting of kinase inhibitors, G protein coupled receptor (GPCR) modulators, epigenic modifiers, histone deacetylases (HDAC) modulators, hedgehog signaling pathway modulators, neuropeptides, dopamine receptor modulators, serotonin receptor modulators, histamine receptor modulators, adenosine receptor agonists, ionophores, ion channel modulators, gamma-secretase modulators, corticosteroids, and any combinations thereof. Examples of proliferation enhancers include, but are not limited to, those described in PCT/US2017/016099, which is incorporated herein by reference. The compound may induce, enhance, or increase satellite cell proliferation by at least 5%, 10%, 20%, 30%, 40%, 50%, 50%, 70%, 80%, 90%, 1-fold, 1.1-fold, 1.5-fold, 2-fold, 3-fold, 4-fold, 5-fold, 10-fold, 50-fold, 100-fold or more relative to an untreated satellite cell.

Compositions Comprising Satellite Cells

Some embodiments of the present invention relate to cell compositions, such as cell cultures or cell populations, comprising satellite cells, wherein the satellite cells have been derived from at least one myoblast. In some embodiments, the cell compositions comprise myoblasts. In some embodiments, the cell compositions comprise differentiated skeletal muscle cells. In some embodiments, the cell compositions comprise proliferative myogenic cells.

In accordance with certain embodiments, the chemically induced satellite cells are mammalian cells, and in a preferred embodiment, such satellite cells are human satellite cells. In some embodiments, the myoblasts have been derived from embryonic muscle cells. In other embodiments, the myoblasts have been isolated from skeletal muscle of a subject.

Other embodiments of the present invention relate to compositions, such as an isolated cell population or cell culture, comprising satellite cells produced by the methods as disclosed herein. In such embodiments, the satellite cells comprise less than about 90%, less than about 85%, less than about 80%, less than about 75%, less than about 70%, less than about 65%, less than about 60%, less than about 55%, less than about 50%, less than about 45%, less than about 40%, less than about 35%, less than about 30%, less than about 25%, less than about 20%, less than about 15%, less than about 12%, less than about 10%, less than about 8%, less than about 6%, less than about 5%, less than about 4%, less than about 3%, less than about 2% or less than about 1% of the total cells in the satellite cells population. In some embodiments, the composition comprises a population of satellite cells which make up more than about 90% of the total cells in the cell population, for example about at least 95%, or at least 96%, or at least 97%, or at least 98% or at least about 99%, or about at least 100% of the total cells in the cell population are satellite cells.

Compositions and Kits

Described herein are kits for practicing methods disclosed herein and for making satellite cells disclosed herein. Also described herein are kits for treating muscle injury. In one aspect, a kit includes at least one myoblast and at least one medium as described herein, and optionally, the kit can further comprise instructions for converting at least one myoblast to a population of satellite cells using a method described herein. In some embodiments, the kit comprises at least two mediums. In some embodiments, the kit comprises at least three mediums. In some embodiments, the kit comprises at least one supplemental agent. In some embodiments, the kit comprises at least two supplemental agents. In some embodiments, the kit comprises at least three supplemental agents. In some embodiments, the kit comprises mediums and/or supplemental agents for dedifferentiating myoblasts to satellite cells. In some embodiments, the kit comprises any combination of mediums and/or supplemental agents, e.g., for dedifferentiating myoblasts to satellite cells.

In some embodiments, the kit comprises at least one myoblast medium. In some embodiments, the kit comprises at least one spin medium. In some embodiments, the kit comprises at least one differentiation medium. In some embodiments, the kit comprises a myoblast medium, a spin medium, and a differentiation medium. In some embodiments, the kit comprises a compound selected from the group consisting of kinase inhibitors, G protein coupled receptor (GPCR) modulators, histone deacetylases (HDAC) modulators, hedgehog signaling pathway modulators, neuropeptides, dopamine receptor modulators, serotonin receptor modulators, histamine receptor modulators, ionophores, ion channel modulators, gamma-secretase modulators, and any combinations thereof.

In some embodiment, the compound in the kit can be provided in a watertight or gas tight container which in some embodiments is substantially free of other components of the kit. The compound can be supplied in more than one container, e.g., it can be supplied in a container having sufficient reagent for a predetermined number of reactions e.g., 1, 2, 3 or greater number of separate reactions to induce myoblasts to satellite cells. A medium and/or supplemental agent can be provided in any form, e.g., liquid, dried or lyophilized form. It is preferred that a compound(s) (e.g., medium or agent) described herein be substantially pure and/or sterile. When a compound(s) described herein is provided in a liquid solution, the liquid solution preferably is an aqueous solution, with a sterile aqueous solution being preferred. When a compound(s) described herein is provided as a dried form, reconstitution generally is by the addition of a suitable solvent. The solvent, e.g., sterile water or buffer, can optionally be provided in the kit.

In some embodiments, the kit further optionally comprises information material. The informational material can be descriptive, instructional, marketing or other material that relates to the methods described herein and/or the use of a compound(s) described herein for the methods described herein.

The informational material of the kits is not limited in its instruction or informative material. In one embodiment, the informational material can include information about production of the compound, molecular weight of the compound, concentration, date of expiration, batch or production site information, and so forth. In one embodiment, the informational material relates to methods for administering the compound. Additionally, the informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about a compound described herein and/or its use in the methods described herein. Of course, the informational material can also be provided in any combination of formats.

In one embodiment, the informational material can include instructions to administer a compound(s) (e.g., a medium and/or supplemental agent) as described herein in a suitable manner to perform the methods described herein, e.g., in a suitable dose, dosage form, or mode of administration (e.g., a dose, dosage form, or mode of administration described herein) (e.g., to a cell in vitro or a cell in vivo). In another embodiment, the informational material can include instructions to administer a compound(s) described herein to a suitable subject, e.g., a human, e.g., a human having or at risk for a disorder described herein or to a cell in vitro.

In addition to a compound(s) described herein, the composition of the kit can include other ingredients, such as a solvent or buffer, a stabilizer, a preservative, a flavoring agent (e.g., a bitter antagonist or a sweetener), a fragrance or other cosmetic ingredient, and/or an additional agent for treating a condition or disorder described herein. Alternatively, the other ingredients can be included in the kit, but in different compositions or containers than a compound described herein. In such embodiments, the kit can include instructions for admixing a compound(s) described herein and the other ingredients, or for using a compound(s) described herein together with the other ingredients, e.g., instructions on combining the two agents prior to administration.

The kit can include one or more containers for the composition containing at least one medium and/or supplemental agent as described herein. In some embodiments, the kit contains separate containers (e.g., two separate containers for the two agents), dividers or compartments for the composition(s) and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of a compound described herein. For example, the kit includes a plurality of syringes, ampules, foil packets, or blister packs, each containing a single unit dose of a compound described herein. The containers of the kits can be air tight, waterproof (e.g., impermeable to changes in moisture or evaporation), and/or light-tight.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a medical implant device, e.g., packaged for surgical insertion.

The kit can also include a component for the detection of a marker for satellite cells, e.g., for a marker described herein, e.g., a reagent for the detection of satellite cells. Or in some embodiments, the kit can also comprise reagents for the detection of negative markers of satellite cells for the purposes of negative selection of satellite cells or for identification of cells which do not express these negative markers (e.g., satellite cells). The reagents can be, for example, an antibody against the marker or primers for a RT-PCR or PCR reaction, e.g., a semi-quantitative or quantitative RT-PCR or PCR reaction. Such markers can be used to evaluate whether an iPS cell has been produced. If the detection reagent is an antibody, it can be supplied in dry preparation, e.g., lyophilized, or in a solution. The antibody or other detection reagent can be linked to a label, e.g., a radiological, fluorescent (e.g., GFP) or colorimetric label for use in detection. If the detection reagent is a primer, it can be supplied in dry preparation, e.g., lyophilized, or in a solution.

The kit can include satellite cells, e.g., satellite cells derived from the same type of myoblast, for example for the use as a positive cell type control.

Methods of Administering a Cell

In one embodiment, the cells described herein, e.g. a population of satellite cells are transplantable, e.g., a population of satellite cells can be administered to a subject. In some embodiments, the subject who is administered a population of satellite cells is the same subject from whom a myoblast used to dedifferentiate into a satellite cell was obtained (e.g. for autologous cell therapy). In some embodiments, the subject is a different subject. In some embodiments, a subject is suffering from a muscle injury, or is a normal subject. For example, the cells for transplantation (e.g. a composition comprising a population of satellite cells) can be a form suitable for transplantation.

The method can further include administering the cells to a subject in need thereof, e.g., a mammalian subject, e.g., a human subject. The source of the cells can be a mammal, preferably a human. The source or recipient of the cells can also be a non-human subject, e.g., an animal model. The term "mammal" includes organisms, which include mice, rats, cows, sheep, pigs, rabbits, goats, horses, monkeys, dogs, cats, and preferably humans. Likewise, transplantable cells can be obtained from any of these organisms, including a non-human transgenic organism. In one embodiment, the transplantable cells are genetically engineered, e.g., the cells include an exogenous gene or have been genetically engineered to inactivate or alter an endogenous gene.

A composition comprising a population of satellite cells can be administered to a subject using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6): 563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

Pharmaceutical Compositions

For administration to a subject, a cell population produced by the methods as disclosed herein, e.g. a population of satellite cells (produced by contacting at least one myoblast with at least one medium (e.g., a myoblast medium, a spin medium, and/or a differentiation medium as described herein) can be administered to a subject, for example in pharmaceutically acceptable compositions. These pharmaceutically acceptable compositions comprise a therapeutically-effective amount of a population of satellite cells as described above, formulated together with one or more pharmaceutically acceptable carriers (additives) and/or diluents.

As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally. Additionally, compounds can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. The phrase "therapeutically-effective amount" as used herein in respect to a population of cells means that amount of relevant cells in a population of cells, e.g., satellite cells, or composition comprising satellite cells of the present invention which is effective for producing some desired therapeutic effect in at least a sub-population of cells in an animal at a reasonable benefit/risk ratio applicable to any medical treatment. For example, an amount of a population of satellite cells administered to a subject that is sufficient to produce a statistically significant, measurable change in at least one symptom of muscle injury, such as muscle repair or regeneration, etc. Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents.

As used herein, the term "repair" refers to a process by which the damages of a muscle tissue are alleviated or completely eliminated. In some embodiments, at least one symptom of muscle tissue damage is alleviated by at least 5%, at least 10%, at least 20%, at least 30%, at least 40%, or at least 50%.

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

As used herein, the term "administer" refers to the placement of a composition into a subject by a method or route which results in at least partial localization of the composition at a desired site such that desired effect is produced. Routes of administration suitable for the methods of the invention include both local and systemic administration. Generally, local administration results in more of the administered satellite cells (or proliferation enhancer treated satellite cells) being delivered to a specific location as compared to the entire body of the subject, whereas, systemic administration results in delivery of the satellite to essentially the entire body of the subject. One method of local administration is by intramuscular injection.

In the context of administering a compound treated cell, the term "administering" also include transplantation of such a cell in a subject. As used herein, the term "transplantation" refers to the process of implanting or transferring at least one cell to a subject. The term "transplantation" includes, e.g., autotransplantation (removal and transfer of cell(s) from one location on a patient to the same or another location on the same patient), allotransplantation (transplantation between members of the same species), and xenotransplantation (transplantations between members of different species). Skilled artisan is well aware of methods for implanting or transplantation of cells for muscle repair and regeneration, which are amenable to the present invention. See for example, U.S. Pat. No. 7,592,174 and U.S. Pat. Pub. No. 2005/0249731, content of both of which is herein incorporated by reference.

Satellite cells or compositions comprising same can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection.

As used herein, a "subject" means a human or animal. Usually the animal is a vertebrate such as a primate, rodent, domestic animal or game animal. Primates include chimpanzees, cynomolgous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments of the aspects described herein, the subject is a mammal, e.g., a primate, e.g., a human. The terms, "patient" and "subject" are used interchangeably herein. The terms, "patient" and "subject" are used interchangeably herein. A subject can be male or female.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with autoimmune disease or inflammation. In addition, the methods and compositions described herein can be used to treat domesticated animals and/or pets.

A subject can be one who has been previously diagnosed with or identified as suffering from or having a disorder characterized with muscle damage or muscle atrophy/wasting. A subject may be someone who has been previously diagnosed with or identified as having a muscle degenerative disorder.

In some embodiments of the aspects described herein, the method further comprises diagnosing and/or selecting a subject for muscle damage or muscle atrophy/wasting before treating the subject for muscle repair or regeneration.

In some embodiments, damaged muscle tissue results from sarcopenia. As used herein, the term "sarcopenia" refers to the loss of muscle mass and function that inevitably occurs with aging. Sarcopenia is responsible for decreased levels of physical activity which, in turn, can result in increased body fat and a further loss of muscle. Loss of muscle mass results from a negative net balance between muscle protein synthesis and muscle protein breakdown. The etiology of this loss of skeletal muscle mass and function is not believed to be clear. Reduced levels of physical activity, loss of motor units secondary to changes in the central nervous system, and inadequate protein intake have all been implicated In some embodiments, the damaged muscle tissue results from a physical injury or trauma. The damaged muscle may be skeletal muscle. In some embodiments, the subject has or is otherwise affected by muscle injury, insult, trauma, or disease.

In some embodiments, disease resulting in damaged muscle tissue is a myopathy. Without limitation, myopathy can be a congenital myopathy or an acquired myopathy. Exemplary myopathies include, but are not limited to, dystrophies, myotonia (neuromyotonia), congenital myopathies (e.g., nemaline myopathy, multi/minicore myopathy, centronuclear myopathy (or myotubular myopathy)), mitochondrial myopathies, familial periodic paralysis, inflammatory myopathies, metabolic myopathies (e.g., glycogen storage disease and lipid storage disorder), dermatomyositis, polymyositis inclusion body myositis, myositis ossificans, rhabdomyolysis and myoglobinuirias.

In some embodiments of this and other aspects described herein, myopathy is a dystrophy selected from the group consisting of muscular dystrophy, Duchenne muscular dystrophy, Becker's muscular dystrophy, Reflex sympathetic dystrophy, Retinal dystrophy, Conal dystrophy, Myotonic dystrophy, Corneal dystrophy, and any combinations thereof.

Congenital myopathy is a term sometimes applied to hundreds of distinct neuromuscular disorders that may be present at birth, but it is usually reserved for a group of rare inherited primary muscle disorders that cause hypotonia and weakness at birth or during the neonatal period and, in some cases, delayed motor development later in childhood. Patients suffer from weakness ranging from mild (late childhood onset and ability to walk through adulthood) to severe (respiratory insufficiency and death within the first year of life).

The most common types of congenital myopathy are nemaline myopathy, myotubular myopathy, central core myopathy, congenital fiber type disproportion, and multi-core myopathy. They are distinguished primarily by their histological features, symptoms, and prognosis. Diagnosis is indicated by characteristic clinical findings and confirmed by muscle biopsy.

Examples of specific myopathys include, but are not limited to, those described in PCT/US2017/016099, which is incorporated herein by reference.

A satellite cell composition described herein can be co-administered to a subject in combination with a proliferation enhancer as described herein and/or a pharmaceutically active agent. Exemplary pharmaceutically active compound include, but are not limited to, those found in *Harrison's Principles of Internal Medicine*, 13$^{th}$ Edition, Eds. T. R. Harrison et al. McGraw-Hill N.Y., NY; Physicians' Desk Reference, 50$^{th}$ Edition, 1997, Oradell New Jersey, Medical Economics Co.; Pharmacological Basis of Therapeutics, 8$^{th}$ Edition, Goodman and Gilman, 1990; United States Pharmacopeia, The National Formulary, USP XII NF XVII, 1990; current edition of Goodman and Oilman's *The Pharmacological Basis of Therapeutics*; and current edition of *The Merck Index*, the complete content of all of which are herein incorporated in its entirety.

In some embodiments of the aspects described herein, the pharmaceutically active agent is a growth factor. Exemplary growth factors include, but are not limited to, basic epidermal growth factor (bEGF), fibroblast growth factors (FGF), FGF-1, FGF-2 (bFGF), FGF-4, thymosins, platelet-derived growth factors (PDGF), epidermal growth factor (EGF), transforming growth factor (TGF), TGF-alpha, TGF-beta, cartilage inducing factors-A and —B, osteoid-inducing factors, osteogenin, bone morphogenic proteins, and other bone growth factors, collagen growth factors, heparin-binding growth factor-1 or -2, and their biologically active derivatives.

The satellite cell composition, proliferation enhancer and/or pharmaceutically active agent can be administered to the subject in the same pharmaceutical composition or in different pharmaceutical compositions (at the same time or at different times). When administered at different times, the satellite cell composition, proliferation enhancer and/or the pharmaceutically active agent can be administered within 5 minutes, 10 minutes, 20 minutes, 60 minutes, 2 hours, 3 hours, 4, hours, 8 hours, 12 hours, 24 hours of administration of the other. When the satellite cell composition, proliferation enhancer and/or the pharmaceutically active agent are administered in different pharmaceutical compositions, routes of administration can be different.

Toxicity and therapeutic efficacy of administration of a compositions comprising a population of satellite cells can be determined by standard pharmaceutical procedures in cell cultures or experimental animals, e.g., for determining the LD50 (the dose lethal to 50% of the population) and the ED50 (the dose therapeutically effective in 50% of the population). Compositions comprising a population of satellite cells that exhibit large therapeutic indices are preferred.

The amount of a composition comprising a population of satellite cells can be tested using several well-established animal models.

In some embodiments, data obtained from the cell culture assays and in animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose of a composition comprising a population of satellite cells can also be estimated initially from cell culture assays. Alternatively, the effects of any particular dosage can be monitored by a suitable bioassay.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

In another aspect of the invention, the methods provide use of an isolated population of satellite cells as disclosed herein. In one embodiment of the invention, an isolated population of satellite cells as disclosed herein may be used for the production of a pharmaceutical composition, for the use in transplantation into subjects in need of treatment, e.g. a subject that has, or is at risk of developing a muscle disease or disorder (e.g., a muscle degenerative disorder). Examples include subjects with muscle atrophy or muscle damage. In one embodiment, an isolated population of satellite cells may be genetically modified. In another aspect, the subject may have or be at risk of muscle damage or muscle atrophy. In some embodiments, an isolated population of satellite cells as disclosed herein may be autologous and/or allogeneic. In some embodiments, the subject is a mammal, and in other embodiments the mammal is a human.

One embodiment of the invention relates to a method of treating muscle injury or disease in a subject comprising administering an effective amount of a composition comprising a population of satellite cells as disclosed herein to a subject with a muscle injury or disease. Other embodiments relate to a method of treating a muscle degenerative disorder in a subject comprising administering an effective amount of a composition comprising a population of satellite cells as disclosed herein to a subject with a muscle degenerative disorder. In a further embodiment, the invention provides a method for treating muscle disease, comprising administering a composition comprising a population of satellite cells as disclosed herein to a subject that has, or has increased risk of developing muscle disease.

In some embodiments, a population of satellite cells as disclosed herein may be administered in any physiologically acceptable excipient, where the satellite cells may find an appropriate site for replication, proliferation, and/or engraftment. In some embodiments, a population of satellite cells as disclosed herein can be introduced by injection, catheter, or the like. In some embodiments, a population of satellite cells as disclosed herein can be frozen at liquid nitrogen temperatures and stored for long periods of time, being capable of use on thawing. If frozen, a population of satellite cells will usually be stored in a 10% DMSO, 50% FCS, 40% RPMI 1640 medium. Once thawed, the cells may be expanded by use of growth factors and/or feeder cells associated with culturing satellite cells as disclosed herein.

In some embodiments, a population of satellite cells as disclosed herein can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. Choice of the cellular excipient and any accompanying elements of the composition comprising a population of satellite cells as disclosed herein will be adapted in accordance with the route and device used for administration. In some embodiments, a composition comprising a population of satellite cells can also comprise or be accompanied with one or more other ingredients that facilitate the engraftment or functional mobilization of the satellite cells. Suitable ingredients include matrix proteins that support or promote adhesion of the satellite cells, or complementary cell types. In another embodiment, the composition may comprise resorbable or biodegradable matrix scaffolds.

Gene therapy can be used to either modify a cell to replace a gene product, to facilitate regeneration of tissue, to treat disease, or to improve survival of the cells following implantation into a subject (i.e. prevent rejection).

In some embodiments, a population of satellite cells can be administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement, including but not limited to improved survival rate or more rapid recovery, or improvement or elimination of symptoms and other indicators as are selected as appropriate measures by those skilled in the art. A population of satellite cells can be administered to a subject at the following locations: clinic, clinical office, emergency department, hospital ward, intensive care unit, operating room, catheterization suites, and radiologic suites.

In other embodiments, a population of satellite cells is stored for later implantation/infusion. A population of satellite cells may be divided into more than one aliquot or unit such that part of a population of satellite cells is retained for later application while part is applied immediately to the subject. Moderate to long-term storage of all or part of the cells in a cell bank is also within the scope of this invention, as disclosed in U.S. Patent Publication No. 2003/0054331 and Patent Publication No. WO 03/024215, and is incorporated by reference in their entireties. At the end of processing, the concentrated cells may be loaded into a delivery device, such as a syringe, for placement into the recipient by any means known to one of ordinary skill in the art.

In some embodiments a population of satellite cells can be applied alone or in combination with other cells, tissue, tissue fragments, growth factors such as VEGF and other known angiogenic or arteriogenic growth factors, biologically active or inert compounds, resorbable plastic scaffolds, or other additive intended to enhance the delivery, efficacy, tolerability, or function of the population. In some embodiments, a population of satellite cells may also be modified by insertion of DNA or by placement in cell culture in such a way as to change, enhance, or supplement the function of the cells for derivation of a structural or therapeutic purpose. For example, gene transfer techniques for stem cells are known by persons of ordinary skill in the art, as disclosed in (Morizono et al., 2003; Mosca et al., 2000), and may include viral transfection techniques, and more specifically, adeno-associated virus gene transfer techniques, as disclosed in (Walther and Stein, 2000) and (Athanasopoulos et al., 2000). Non-viral based techniques may also be performed as disclosed in (Murarnatsu et al., 1998).

In another aspect, in some embodiments, a population of satellite cells could be combined with a gene encoding pro-angiogenic growth factor(s). Genes encoding anti-apoptotic factors or agents could also be applied. Addition of the gene (or combination of genes) could be by any technology known in the art including but not limited to adenoviral transduction, "gene guns," liposome-mediated transduction, and retrovirus or lentivirus-mediated transduction, plasmid adeno-associated virus. Cells could be implanted along with a carrier material bearing gene delivery vehicle capable of releasing and/or presenting genes to the cells over time such that transduction can continue or be initiated. Particularly when the cells and/or tissue containing the cells are administered to a patient other than the patient from whom the cells and/or tissue were obtained, one or more immunosuppressive agents may be administered to the patient receiving the cells and/or tissue to reduce, and preferably prevent, rejection of the transplant. As used herein, the term "immunosuppressive drug or agent" is intended to include pharmaceutical agents which inhibit or interfere with normal immune function. Examples of immunosuppressive agents suitable with the methods disclosed herein include agents that inhibit T-cell/B-cell costimulation pathways, such as agents that interfere with the coupling of T-cells and B-cells via the CTLA4 and B7 pathways, as disclosed in U.S. Patent Publication No 2002/0182211, which is incorporated herein by reference. In one embodiment, a immunosuppressive agent is cyclosporine A. Other examples include myophenylate mofetil, rapamicin, and anti-thymocyte globulin. In one embodiment, the immunosuppressive drug is administered with at least one other therapeutic agent. The immunosuppressive drug is administered in a formulation which is compatible with the route of administration and is administered to a subject at a dosage sufficient to achieve the desired therapeutic effect. In another embodiment, the immunosuppressive drug is administered transiently for a sufficient time to induce tolerance to the satellite cells of the invention.

Pharmaceutical compositions comprising effective amounts of a population of satellite cells are also contemplated by the present invention. These compositions comprise an effective number of satellite cells, optionally, in combination with a pharmaceutically acceptable carrier, additive or excipient. Systemic administration of a population of satellite cells to the subject may be preferred in certain indications, whereas direct administration at the site of or in proximity to the diseased and/or damaged tissue may be preferred in other indications.

In some embodiments, a population of satellite cells can optionally be packaged in a suitable container with written instructions for a desired purpose, such as the reconstitution or thawing (if frozen) of a population of satellite cells prior to administration to a subject.

EXAMPLES

Example 1—Myoblasts Cultured in a 3D Spin Environment Self Assemble into Skeletal Muscle Organoids Composed of Differentiated Skeletal Muscle and a Proliferative Myogenic Population Myoblasts isolated from WT (C57bl/6), MyoDCre ROSATdtomato, Pax7$^{nGFP}$and Pax7Cre ROSATdtomato, when cultured in 3D spin conditions self assemble into 3D spheres (FIG. 1A). To determine the state of differentiation of cells residing within a skeletal muscle organoid we collected spheres at Day 10, Day 20 and Day 30 of growth in 3D conditions. At each time point collected spheres were frozen in OCT:Sucrose and sectioned at 10 μm. Sections were stained with Pax7 (DSHB) to identify myoblasts or satellite cells (Seale et al., 2000) and within an antibody recognizing myosin heavy chain (MyHC, MF20-DSHB) a marker of terminal differentiation for skeletal muscle (Bader et al., 1982). Skeletal muscle organoids at each of the three time points are composed of a combination of Pax7$^+$ and MyHC+ cells with a decreasing percentage of Pax7$^+$ cells with time.

Figure 1B:
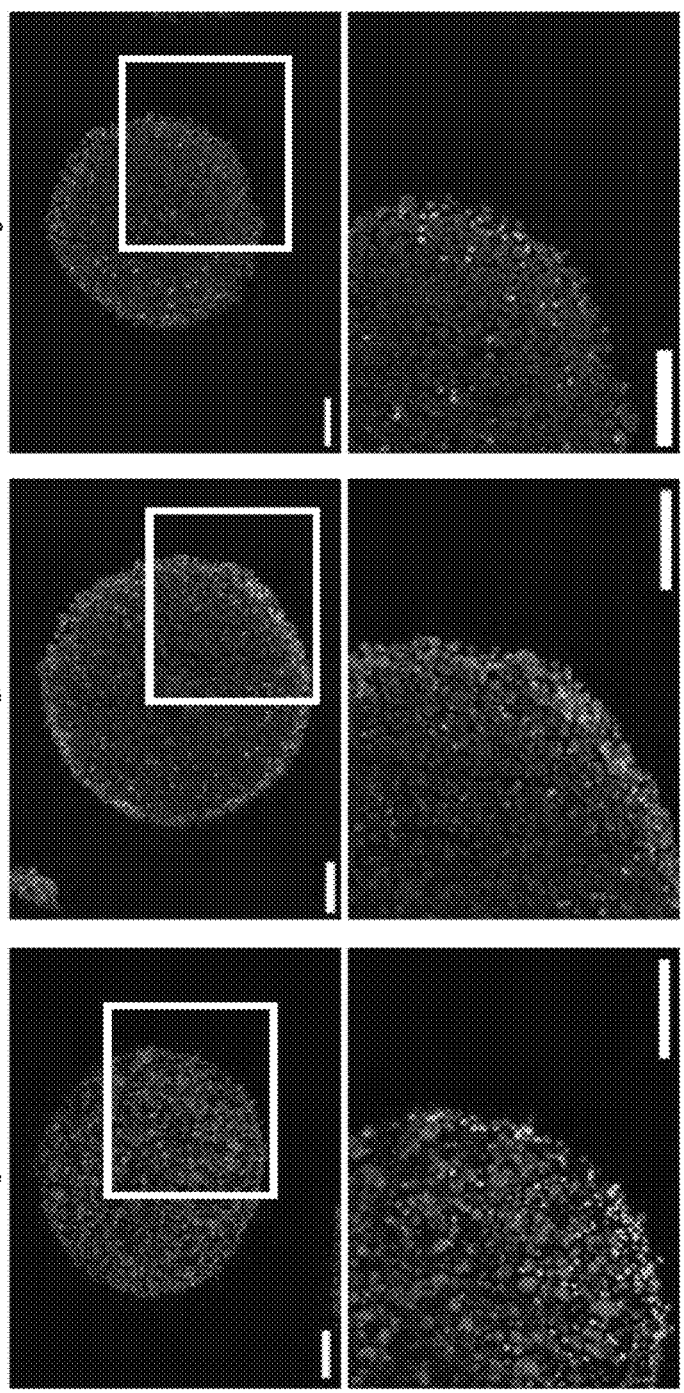
Figure 1D:
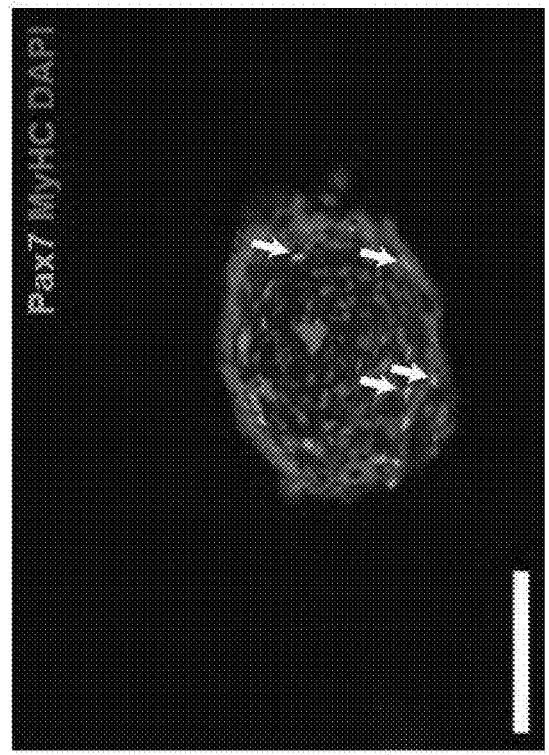
Figure 1C:
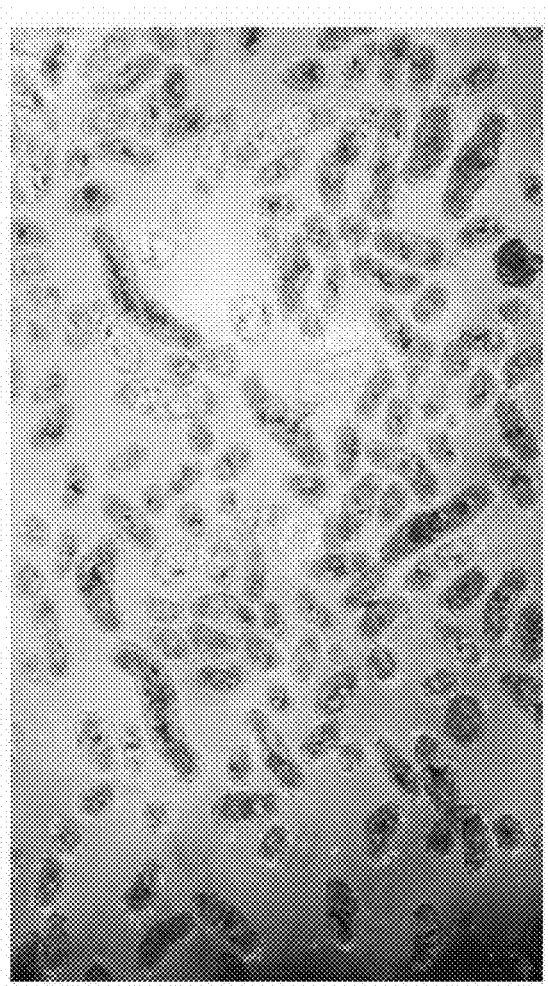

To determine whether this finding holds for human cells we proliferated WT human skeletal myoblasts (Life Technologies #A12555) in myoblasts medium with a higher concentration of bFGF (10 ng/ml). Human myoblasts were seeded into spheroid 96 well microplate (Corning-4515) for a period of 4 days prior to transfer onto a 10 cm low adherence plate maintained on an orbital shaker. Following 10 days of culture human skeletal muscle organoids were formed (FIG. 1B). Cryosectioned human skeletal muscle organoids stained with Pax7 and MyHC display a majority of cells that are MyHC positive. Interestingly, human myoblasts do not express the transcription factor Pax7 during regular culture therefore it is important to note the presence of Pax7 positive human cells present within skeletal muscle organoids (FIG. 1C). Our data suggests that human myoblasts are able to self assemble into 3D spheres when seeded into spheroid plates. Following sphere formation the appearance of Pax7$^+$ human myogenic cells suggests dedifferentiation or reprogramming has occurred to return a myoblast back into a cell that resembles the satellite cell state.

Figure 2A:
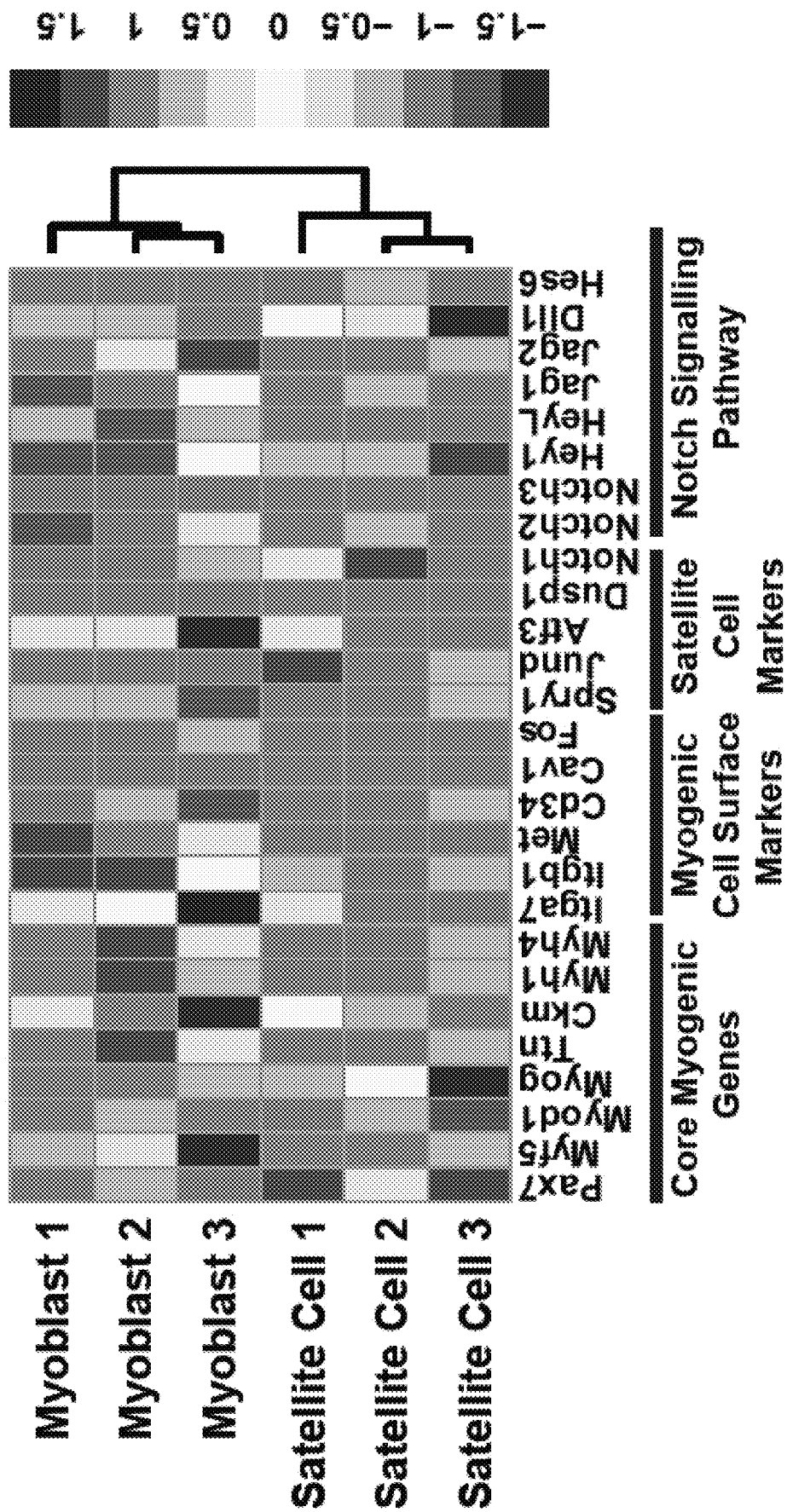
FIGS. 2A-2B depict transcriptional profiling of skeletal muscle organoid derived satellite-like cells.
Figure 2B:
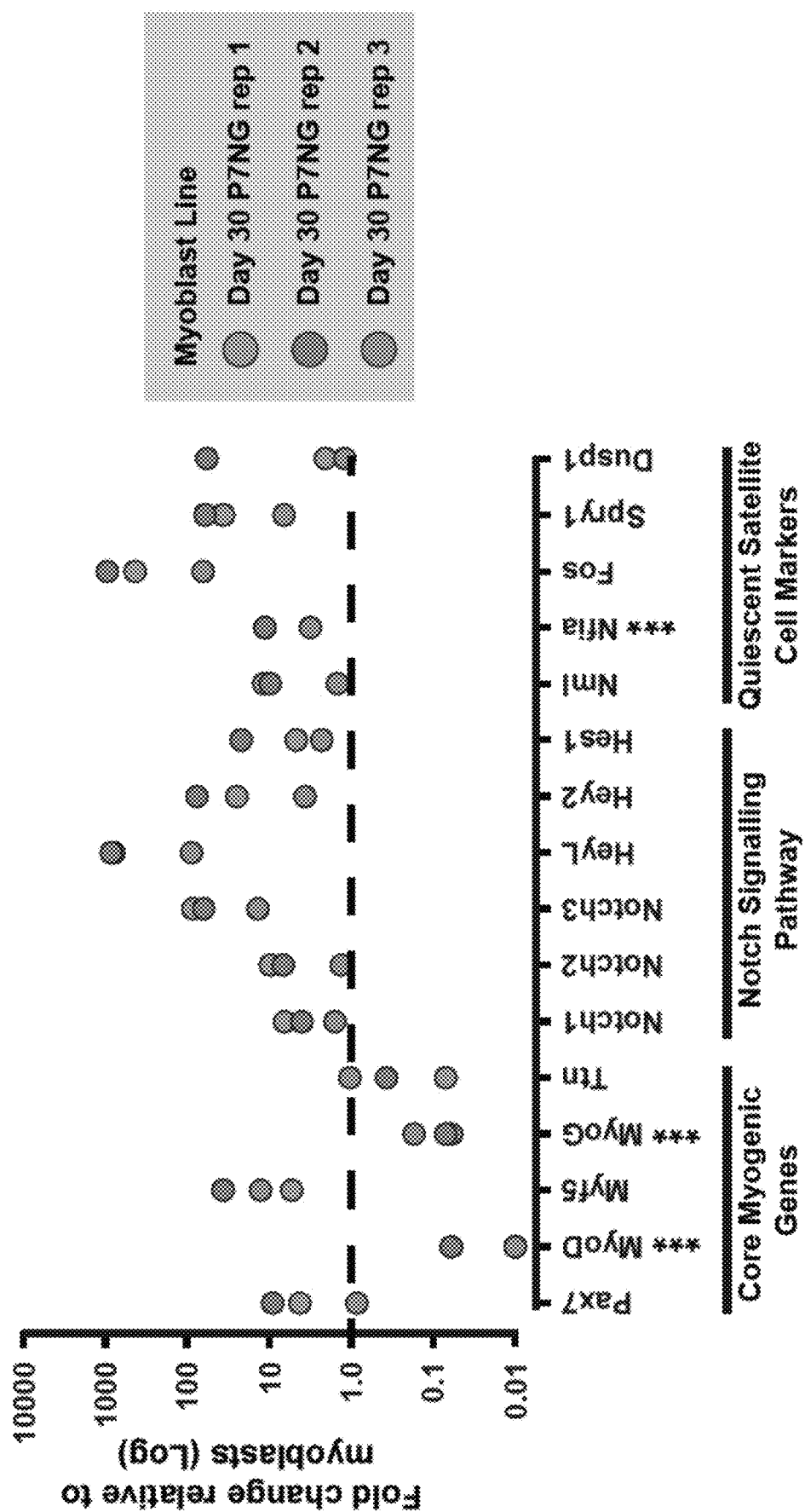

We next conducted RNAseq analysis to identify a transcriptional fingerprint for the satellite cell state (FIG. 2A). Multiple core myogenic genes are highly expressed in satellite cells (Pax7, Myf5) while the master transcription factor for skeletal muscle MyoD is preferentially expressed in myoblasts and absent in satellite cells. These myogenic markers in combination with panels for quiescence related genes (Spry1, Nm1, Nfia, Fos, Dusp1) and members of the Notch signaling pathway (Notch1, 2, 3, HeyL, Hey2, Hes) serve as a transcriptional fingerprint that specifies satellite cells. To determine whether Pax7 positive cells that reside in skeletal muscle organoids share a similar transcriptional profile with the satellite cell we isolated total RNA from nGFP cells purified from 30 day cultured skeletal muscle organoids via fluorescence activated cell sorting (FACS) (FIG. 2B). Following qPCR analysis we determined increases in Pax7 (~4.5 fold) and Myf5 (~18 fold) along with a significant reduction in MyoD (~50 fold). Furthermore, Notch signaling pathway markers Notch1 (~2.5 fold), Notch2 (~4 fold), Notch3 (~35 fold), HeyL (~580 fold), Hey2 (~37 fold) and Hes1 (~11 fold) were increased in nGFP$^+$ day 30 skeletal muscle organoid derived cells. Quiesence related genes or markers of activation were enhanced including Nm1 (~5 fold), Nfia (5 fold), Fos (~480 fold), Spry1 (~34 fold) and Dusp1 (~20 fold) in the nGFP$^+$ cell population from day 30 skeletal muscle organoids (FIG. 2B). This data suggests that nGFP+ cells isolated from skeletal muscle organoids have a transcriptional profile that resembles that of the satellite cell.

Figure 3B:
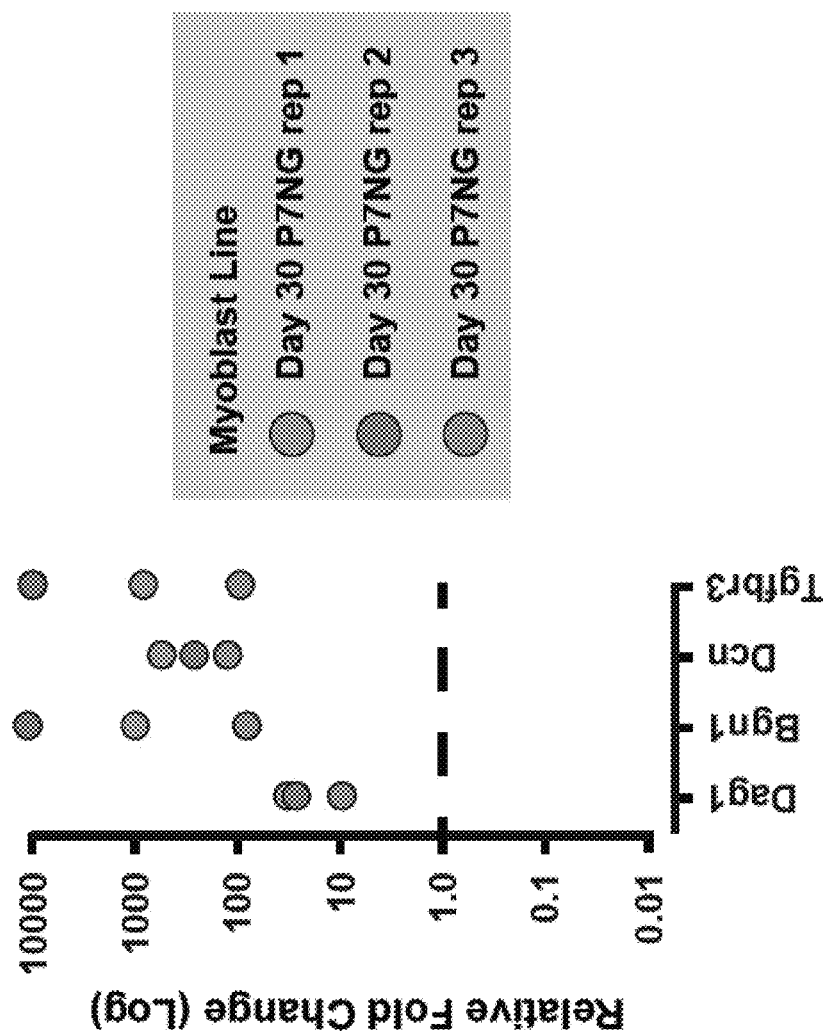
Figure 3A:
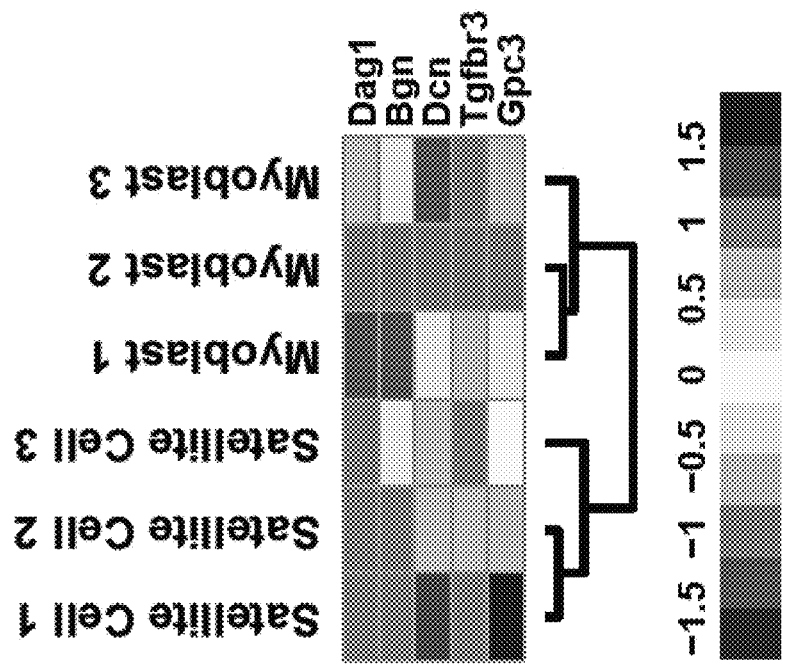
Figure 4A:
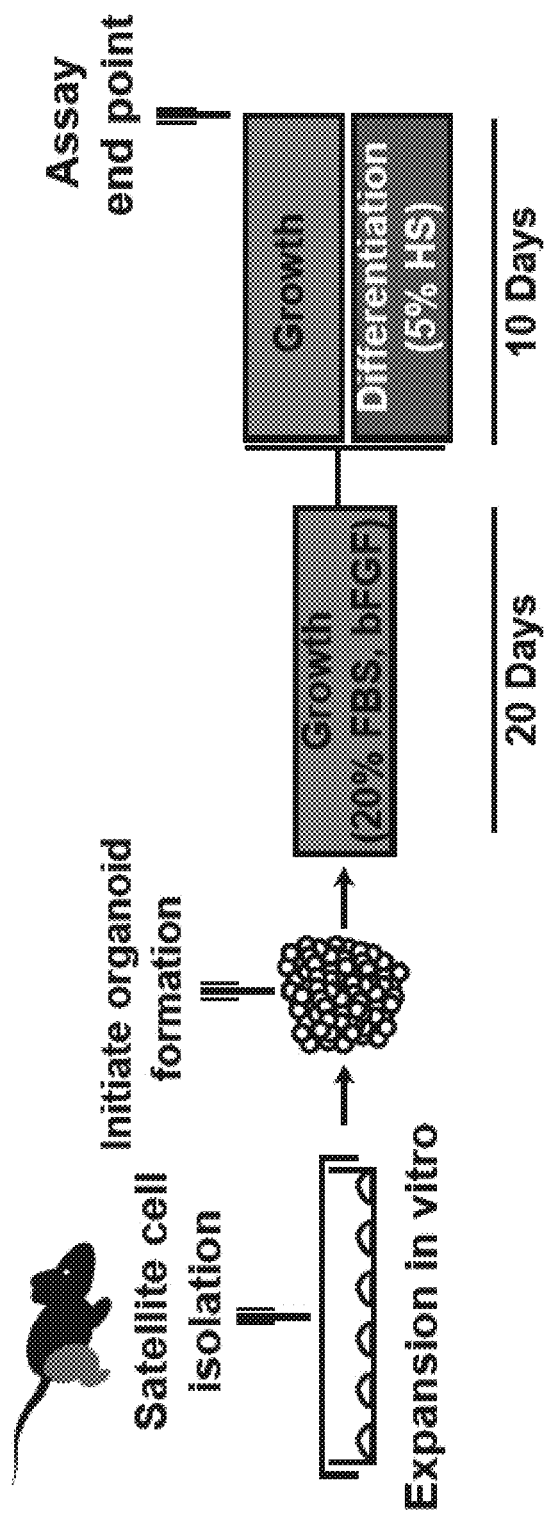
FIGS. 4A-4E demonstrate methods for generating skeletal muscle organoids.
Figure 4C:
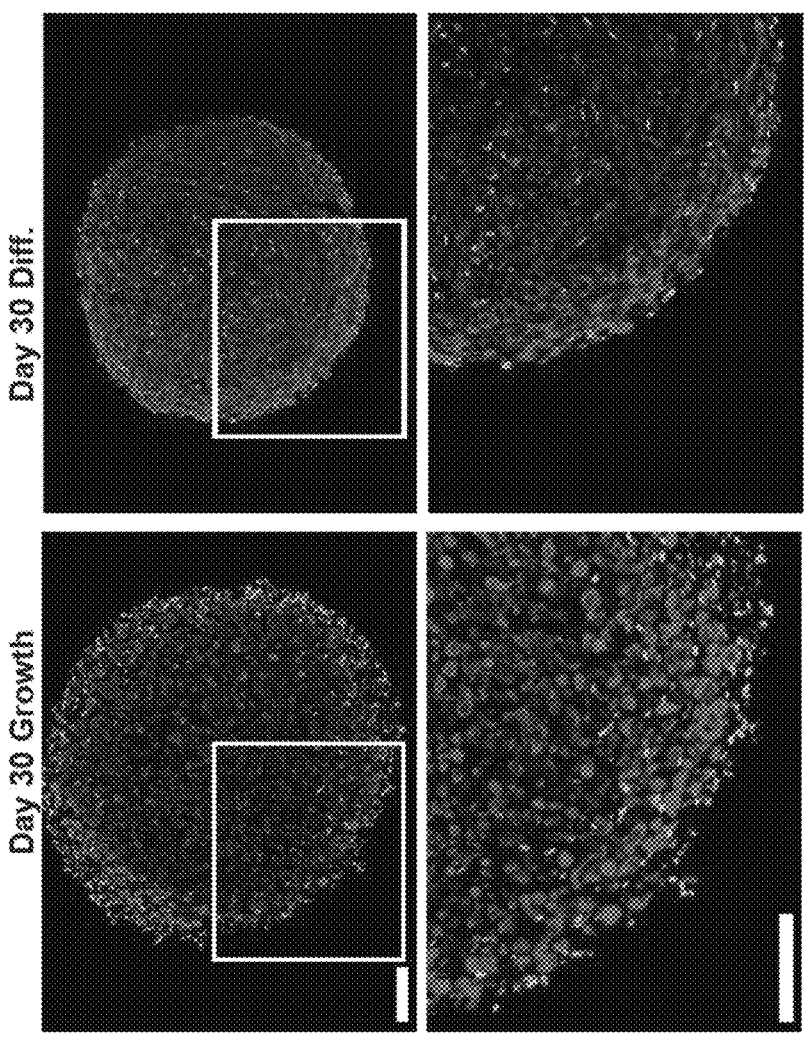
Figure 4B:
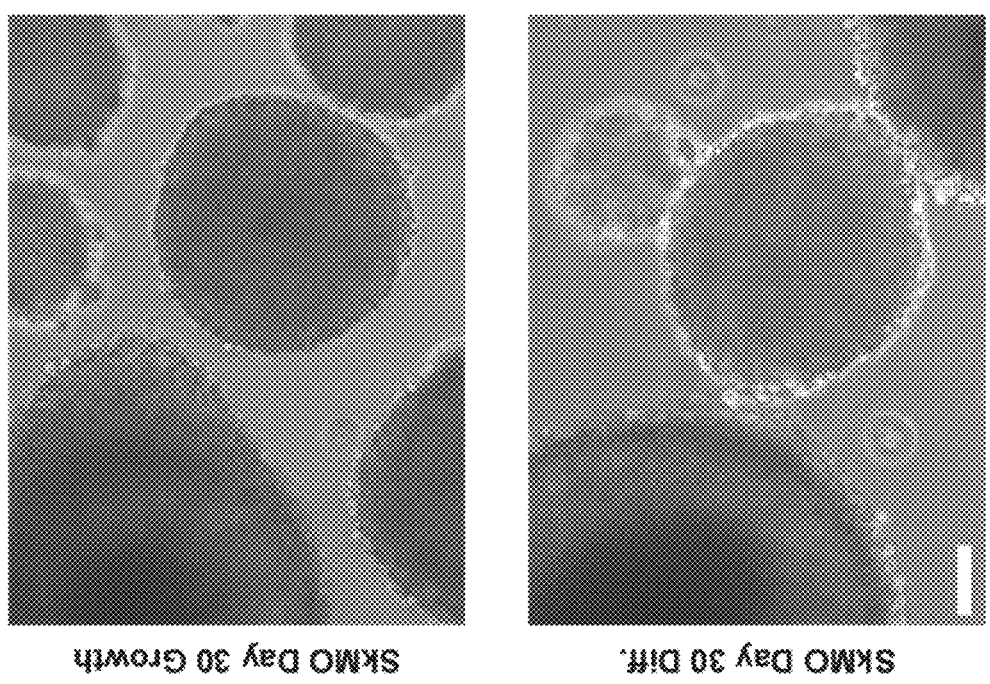
Figure 4D:
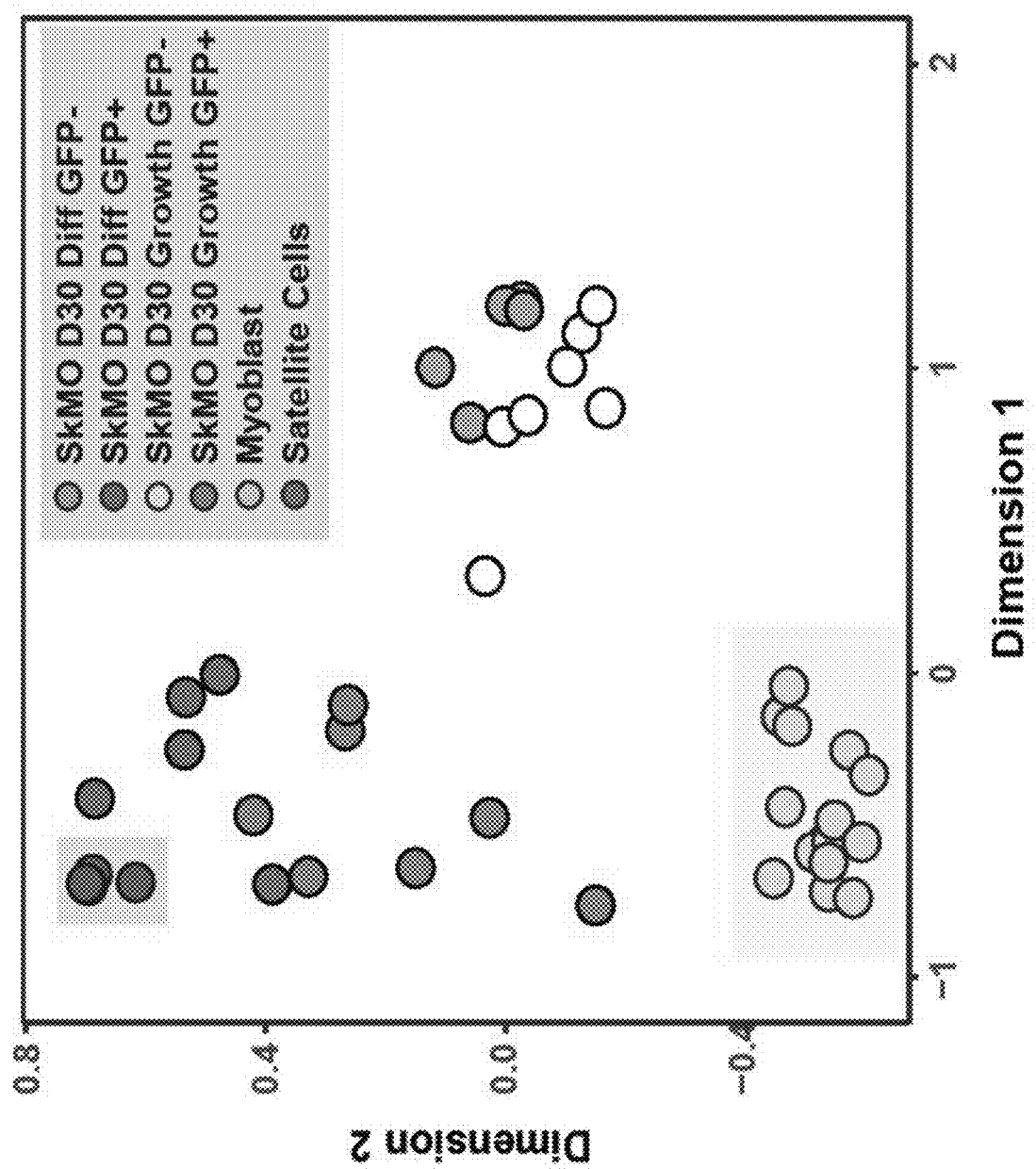
Figure 4E:
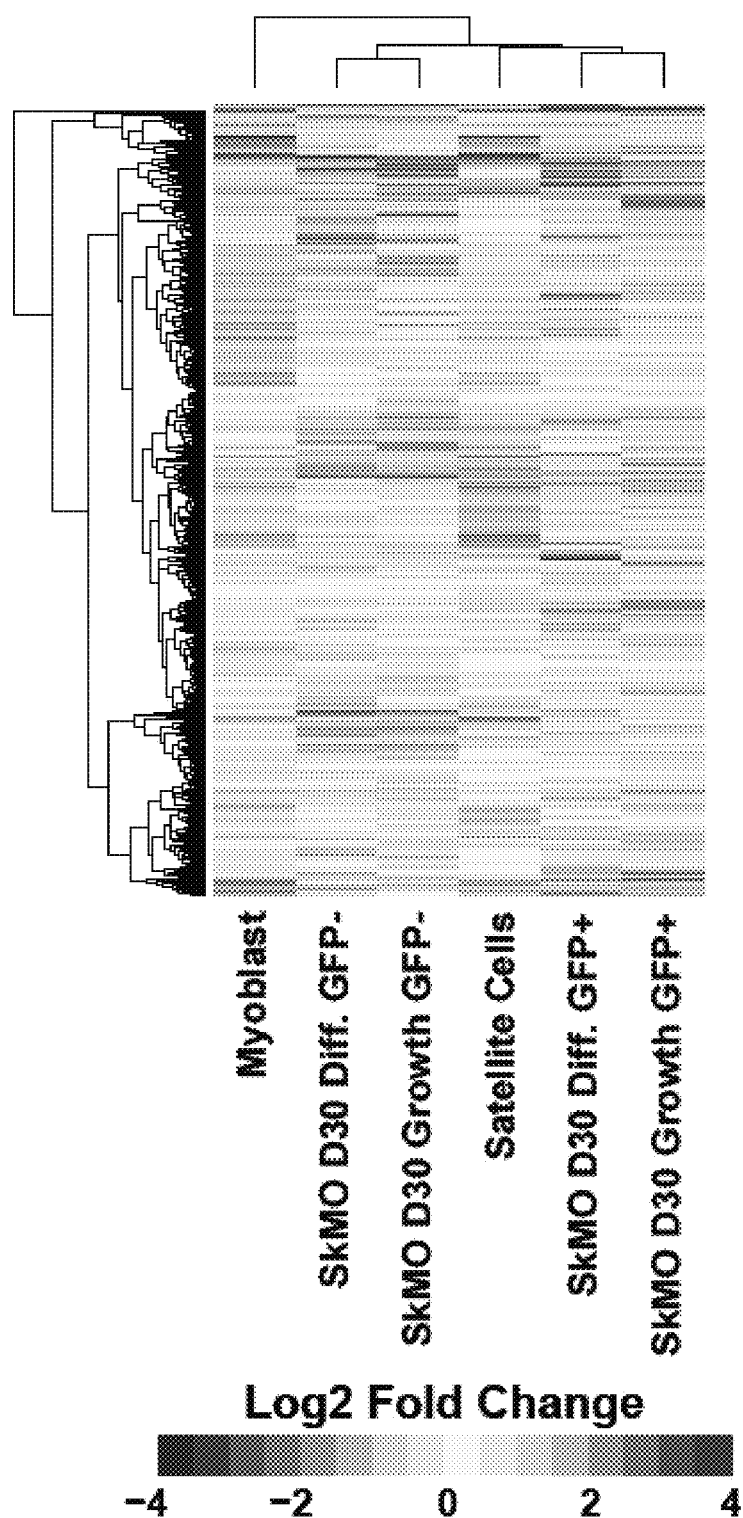
Figures 5A, 5B:
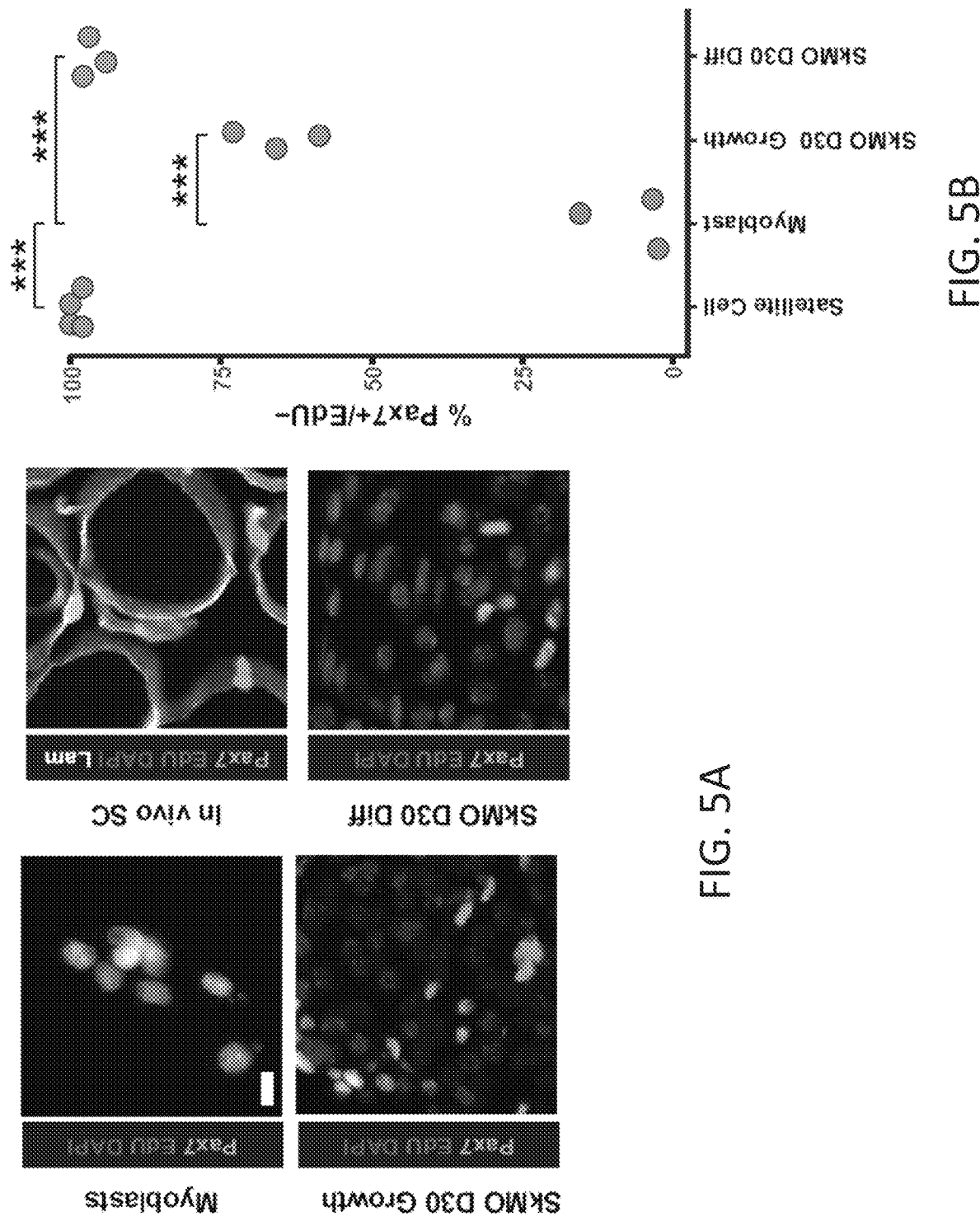
FIGS. 5A-5D provide biomarkers and phenotypic data that shows that skeletal muscle organoid (SkMO) derived cells are similar to endogenous satellite cells.
Figure 5D:
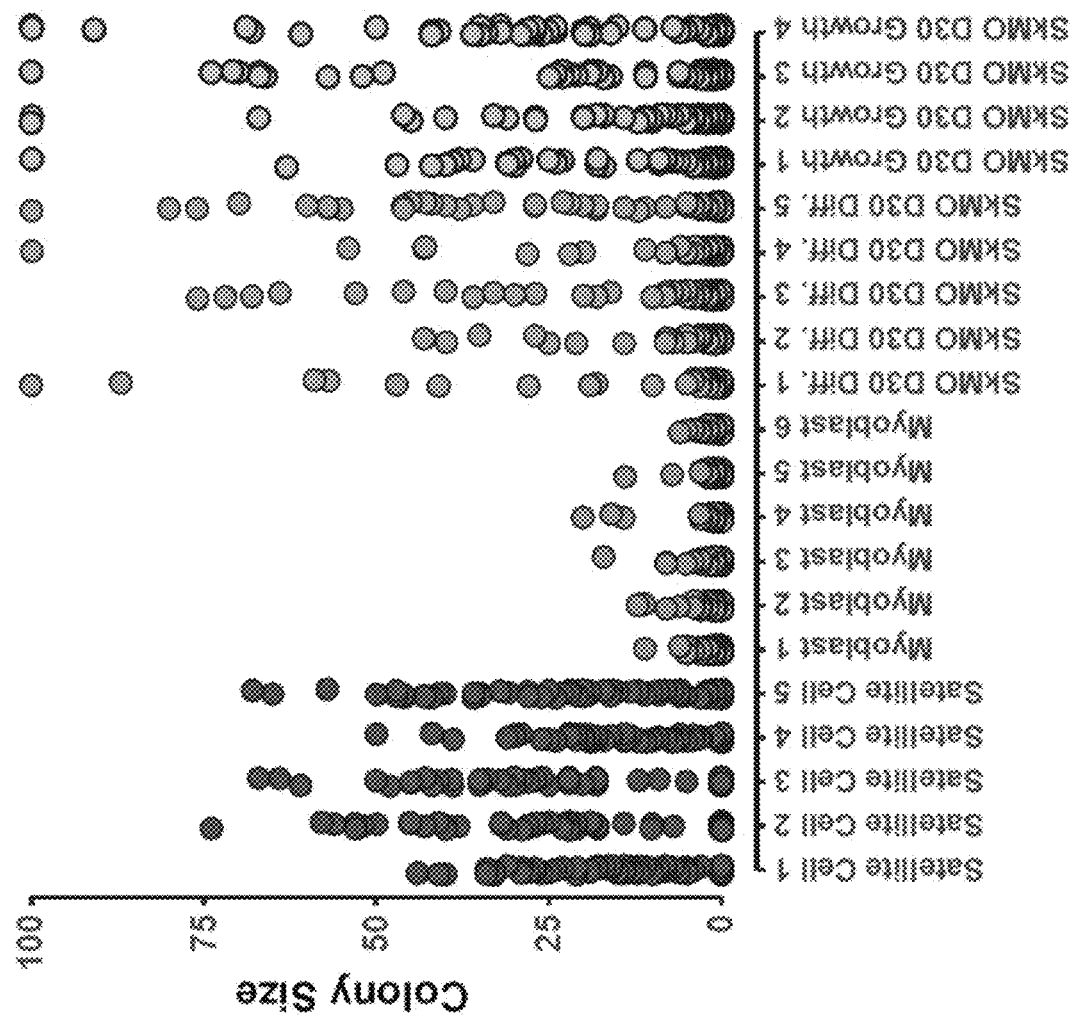
Figure 5C:
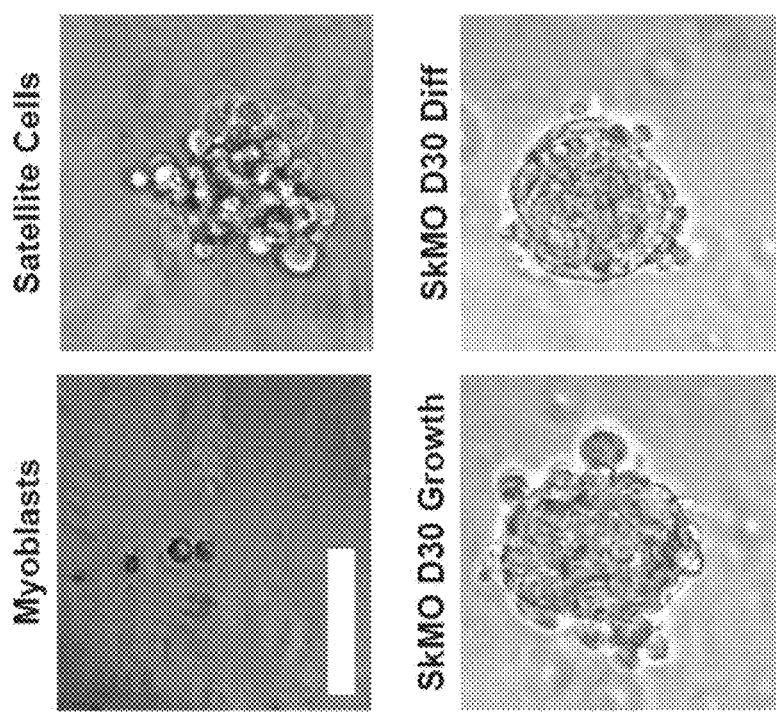
Figure 6A:
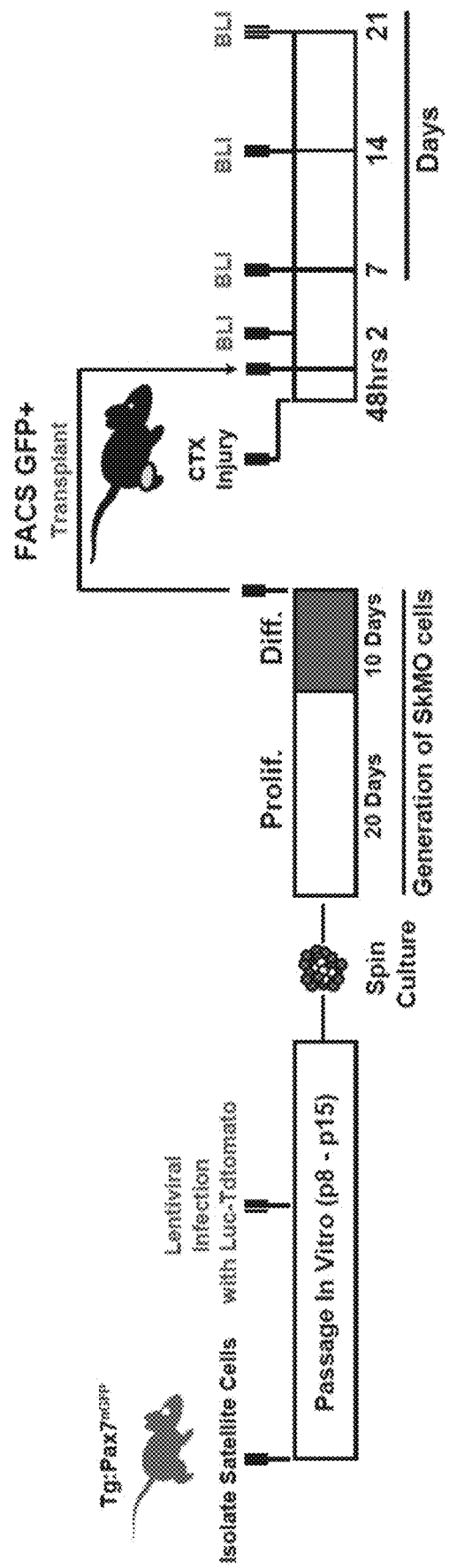
FIGS. 6A-6F provides in vivo data demonstrating that skeletal muscle organoid (SkMO) cells engraft and repopulate following transplant into damaged skeletal muscle.
Figures 6B, 6C:
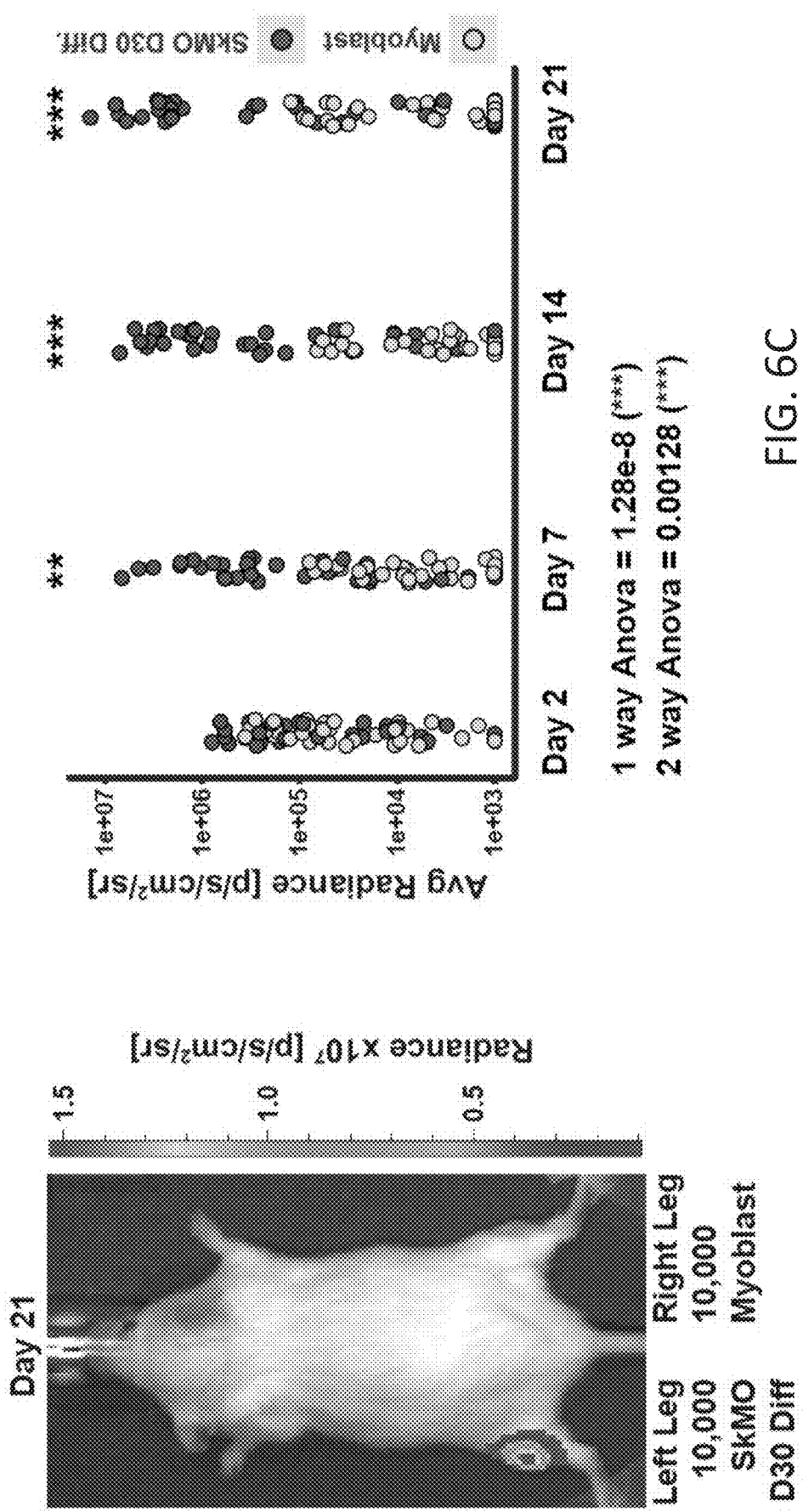
Figures 6E, 6F, 6G:
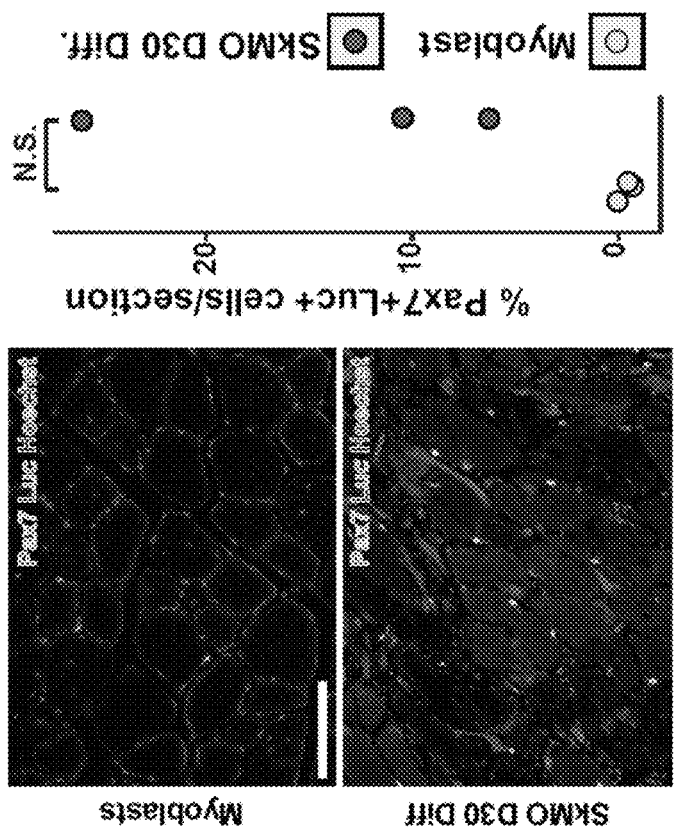
FIG. 6G provides quantification of the repopulation assay (*Note: SkMO cells are not currently significant).
Figure 6D:
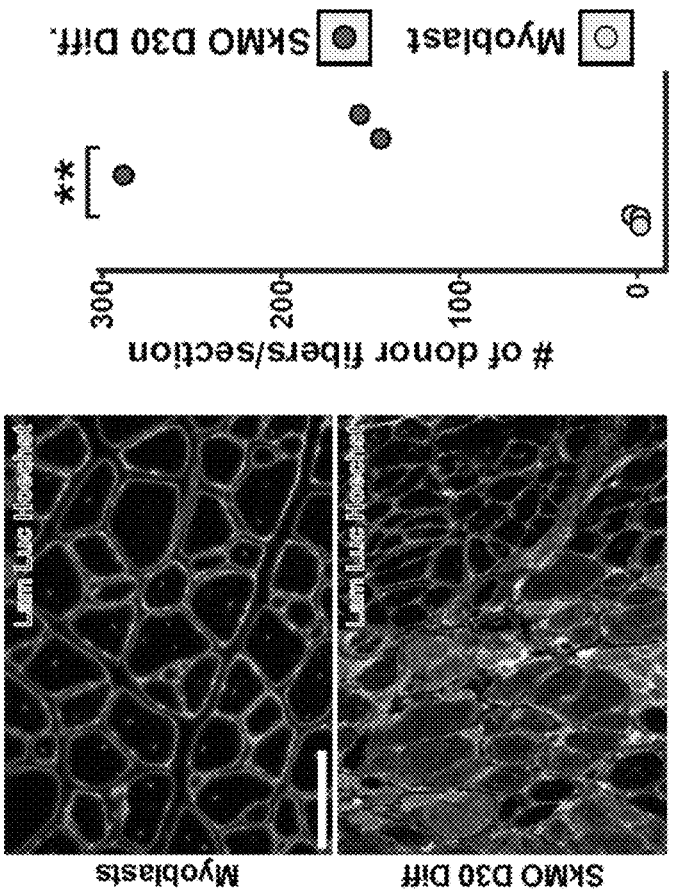
Figure 7A:
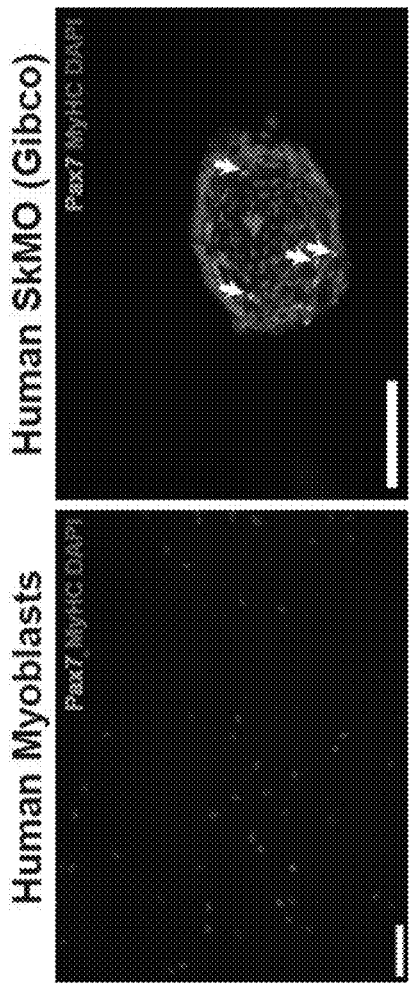
FIGS. 7A-7C provide human data demonstrating that human myoblasts form SkMO cells. The SkMO cells formed from human myoblasts are Pax7 positive (FIG. 7A).
Figure 7B:
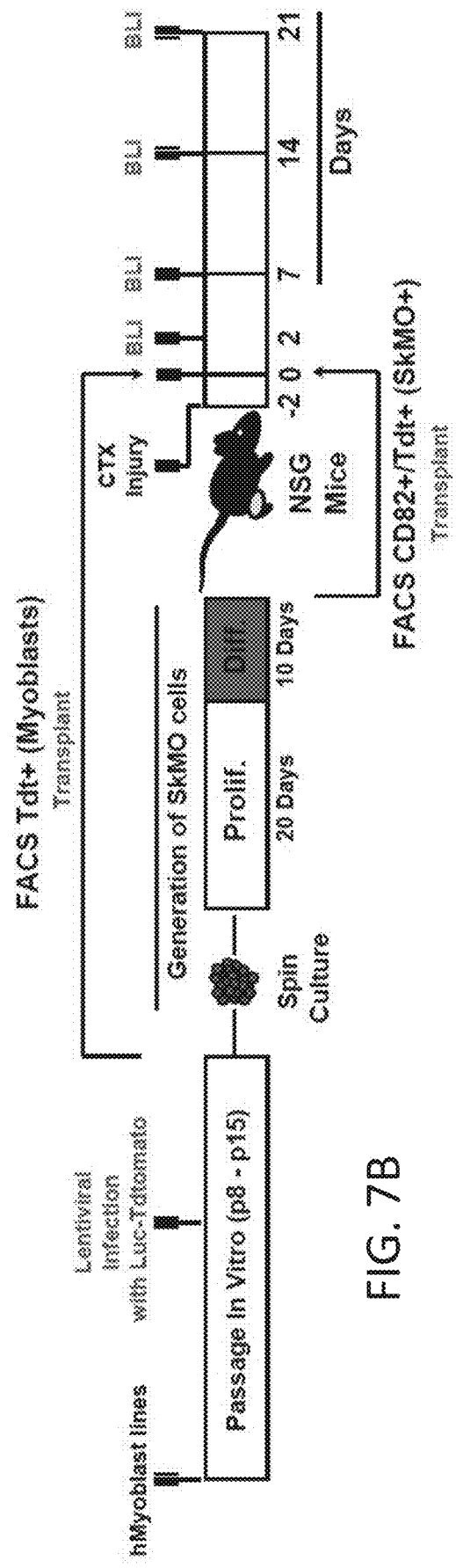
Figure 7C:
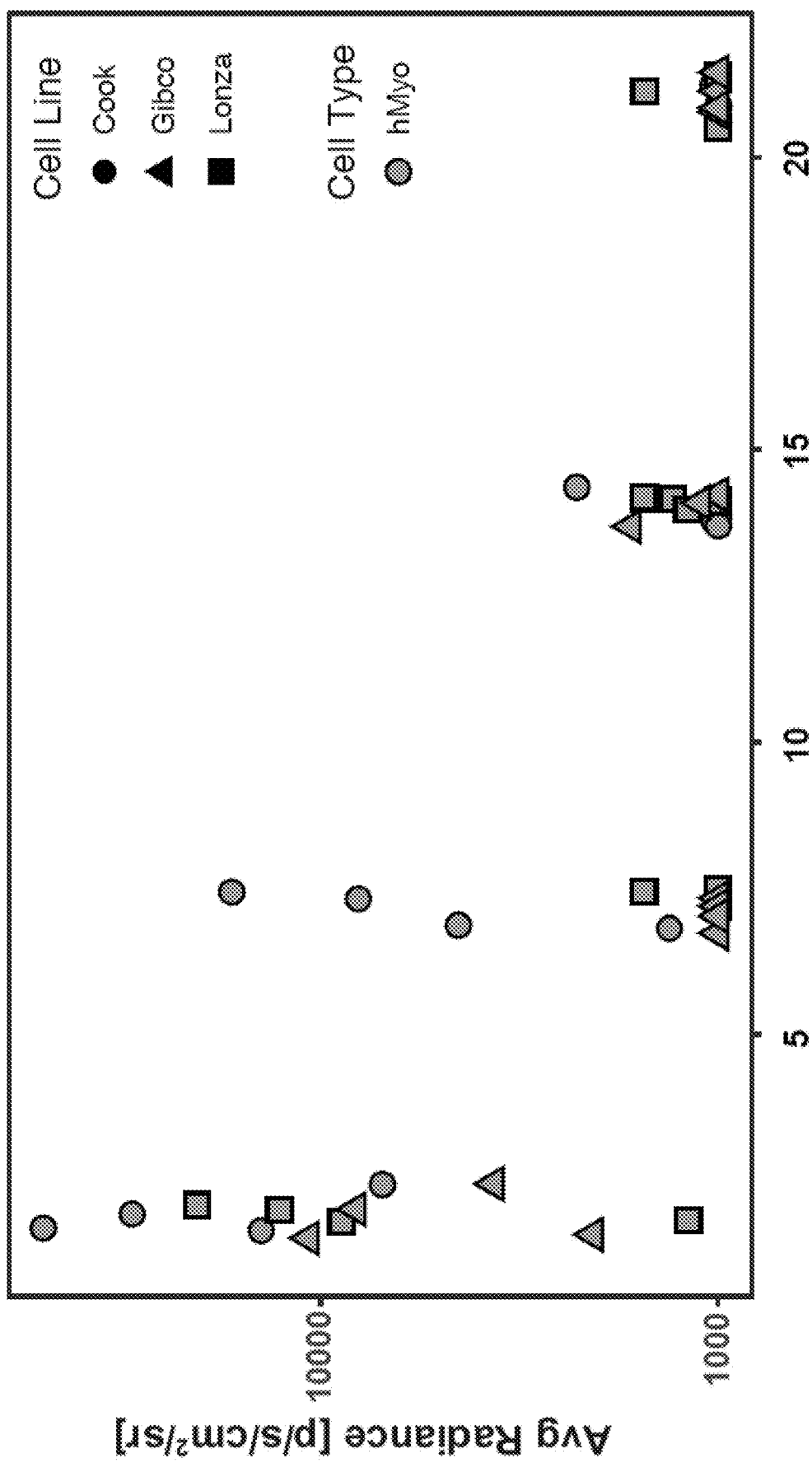
Figure 8E:
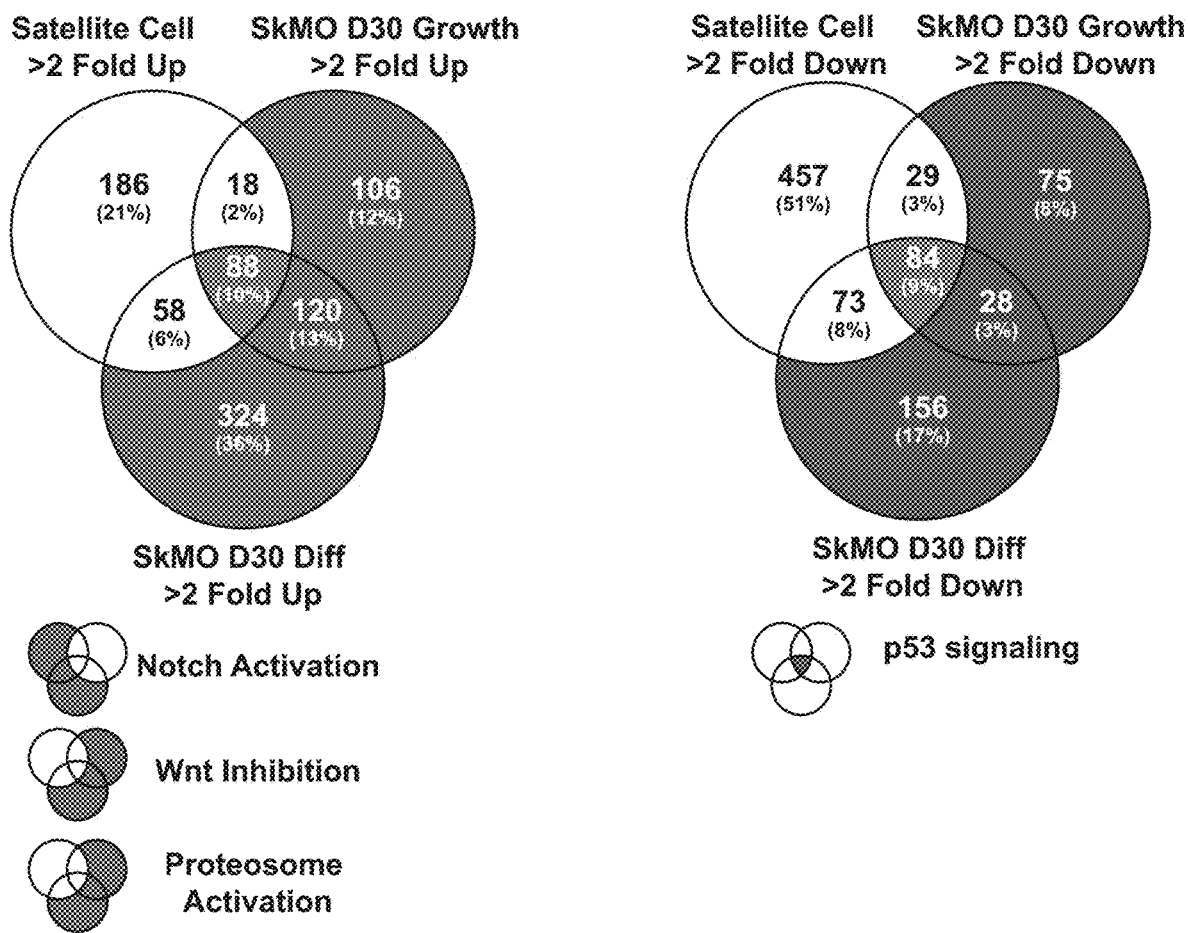

To mechanistically address how skeletal muscle organoids enable myogenic cells to return to the satellite cell state we considered the differences in environment between standard 2D and 3D culture. Adult stem cells possess the capacity to divide asymmetrically thus giving rise to a progenitor population while simultaneously self-renewing to maintain the stem cell pool (Kuang et al., 2007). In order for this to occur, factors within the stem cell niche are critical. We assessed our RNAseq dataset for extracellular molecules that could account for these differences in the niche presented to myoblasts in 2D and 3D culture. Following analysis a core group of proteoglycans emerged that are enriched in satellite cells compared to myoblasts (FIG. 3A). Following 3D culture, nGFP+ cells are highly enriched for these proteoglycan markers (FIG. 3B). To further confirm the presence of these proteoglycans at the protein level we sectioned and stained skeletal muscle organoids cultured for 20 days in spin medium or 10 days in spin medium followed by 10 days in serum free differentiation medium (FIG. 3C). Following differentiation in serum free medium we observed an increase in the presence of Bgn and TgfbrIII (FIG. 3D). Our data suggests that 3D culture more accurately resembles the satellite cell niche in vivo therefore giving rise to cells that resemble satellite cells at the transcriptional profile and secrete proteoglycans critical for establishing the satellite cell niche.

Materials and Methods

Media

Myoblast medium—Ham's F10 (Wisent), 20% heat inactivated fetal bovine serum, 5 ng/ml bFGF (Millipore), 1× Non Essential Amino Acids (Life Technologies), 1× Glutamax (Life Technologies).

Spin medium—DMEM:F12 (Life Technologies), 20% heat inactivated fetal bovine serum, 10 ng/ml bFGF (Millipore), 1× Non Essential Amino Acids (Life Technologies), 1× Glutamax (Life Technologies).

Differentiation medium—DMEM (Life Technologies), 1× Non Essential Amino Acids (Life Technologies), 1× Glutamax (Life Technologies.

Cell Lines

Methods for generating satellite cells were conducted using multiple mouse strains and human lines, including Bl/6, MyoDiCre, Pax7nGFP, Pax7CreROSATdt, Pax7CreROSALuc, and human lines from Gibco and Cook.

Myoblast Expansion

Myoblasts from multiple mouse strains were isolated from hind limb skeletal muscle and cultured on collagen coated dishes in myoblast medium. Myoblast lines were passaged with Trypsin (Life Technologies). Myoblast lines were expanded on 10 cm culture dishes to obtain 10 plates.

Cells were subsequently passaged and seeded onto 10 15 cm plates and cultured until they reached ~80 confluence prior to seeding into spinner flasks.

3D Sphere Formation Conditions

Myoblasts are seeded into a 125 ml spinner flask (Corning) at a density of 1 million cells/ml. Spin speed for the flask is set at 55 rpm. Cultures are fed every two days by removing half of the media and replacing it with fresh media.

Differentiation Conditions

Myoblasts in spin culture (spin medium) formed myospheres or skeletal muscle organoids composed of differentiated and proliferative cells. Following culture in serum free conditions (differentiation medium) the proliferative myogenic cells quiesce and return to a satellite cell state. Skeletal muscle organoids are grown in spin medium for a duration of 20 days. Differentiation is conducted for 10 days.

REFERENCES

Bader, D., Masaki, T., and Fischman, D. A. (1982). Immunochemical analysis of myosin heavy chain during avian myogenesis in vivo and in vitro. J Cell Biol 95, 763-770.

Collins, C. A., Olsen, I., Zammit, P. S., Heslop, L., Petrie, A., Partridge, T. A., and Morgan, J. E. (2005). Stem cell function, self-renewal, and behavioral heterogeneity of cells from the adult muscle satellite cell niche. Cell 122, 289-301.

Kuang, S., Kuroda, K., Le Grand, F., and Rudnicki, M. A. (2007). Asymmetric self-renewal and commitment of satellite stem cells in muscle. Cell 129, 999-1010. Mauro, A. (1961). Satellite cell of skeletal muscle fibers. J Biophys Biochem Cytol 9, 493-495.

Montarras D., Morgan J., Collins C., Relaix F., Zaffran S., Cumano A., Partridge T., Buckingham M. Direct isolation of satellite cells for skeletal muscle regeneration. Science. 2005; 309:2064-2067.

Price, F. D., Kuroda, K., and Rudnicki, M. A. (2007). Stem cell based therapies to treat muscular dystrophy. Biochim Biophys Acta 1772, 272-283.

Seale, P., Sabourin, L. A., Girgis-Gabardo, A., Mansouri, A., Gruss, P., and Rudnicki, M. A. (2000). Pax7 is required for the specification of myogenic satellite cells. Cell 102, 777-786.

Yin, H., Price, F., and Rudnicki, M. A. (2013). Satellite cells and the muscle stem cell niche. Physiol Rev 93, 23-67.

What is claimed is:

1. A method for engraftment of non-naturally occurring satellite cells for treating a muscle disorder, the method comprising administering to a subject in need thereof a pharmaceutical composition comprising therapeutically effective amount of an isolated population of non-naturally occurring satellite cells, wherein:
the non-naturally occurring satellite cells have a gene expression profile that is different from the gene expression profile of an endogenous satellite cell;
the non-naturally occurring satellite cells express two or more genes selected from the group consisting of: Nr2f1, Dmpl, Wisp2/Ccn5, Ecm1, Mgp, Igfbp5, Itgb5, Sdc2 and Bgn, wherein the expression of the two or more genes is upregulated by greater than 2-fold relative to expression by myoblasts and the two or more genes are not expressed in an endogenous satellite cell;
the non-naturally occurring satellite cells have capacity to repopulate the satellite cell niche; and
the non-naturally occurring satellite cells cause muscle regeneration following transplantation.

2. The method of claim 1, wherein the non-naturally occurring satellite cells are derived from a dedifferentiated myoblast.

3. The method of claim 1, wherein the non-naturally occurring satellite cells are expandable in culture.

4. The method of claim 1, wherein the non-naturally occurring satellite cells exhibit a response to a muscle injury.

5. The method of claim 1, wherein the non-naturally occurring satellite cells exhibit morphology that resembles the morphology of an endogenous satellite cell.

6. The method of claim 1, wherein the non-naturally occurring satellite cells further express at least one quiescence-related gene.

7. The method of claim 1, wherein the non-naturally occurring satellite cells further express at least one Notch signaling pathway gene.

8. The method of claim 1, wherein the non-naturally occurring satellite cells further express Myf5 and/or Pax7.

9. The method of claim 1, wherein the non-naturally occurring cells do not express MyoD.

10. The method of claim 1, wherein the non-naturally occurring satellite cells are encapsulated in a microcapsule.

11. The method of claim 1, wherein the subject has, or has an increased risk of developing, a muscle degenerative disorder.

12. The method of claim 1, wherein the subject has, or has an increased risk of developing, muscle trauma.

13. The method of claim 1, wherein the subject has, or has an increased risk of developing, muscle atrophy.

14. A method for treatment of a muscle disorder in a subject in need thereof, the method comprising administering to the subject a pharmaceutical composition comprising therapeutically effective amount of an isolated population of non-naturally occurring satellite cells, wherein:
the non-naturally occurring satellite cells have a gene expression profile that is different from the gene expression profile of an endogenous satellite cell;
the non-naturally occurring satellite cells express two or more genes selected from the group consisting of: Nr2f1, Dmpl, Wisp2/Ccn5, Ecm1, Mgp, Igfbp5, Itgb5, Sdc2 and Bgn, wherein the expression of the two or more genes is upregulated by greater than 2-fold relative to expression by myoblasts and the two or more genes are not expressed in an endogenous satellite cell;
the non-naturally occurring satellite cells have capacity to repopulate the satellite cell niche; and
the non-naturally occurring satellite cells cause muscle regeneration following transplantation.

15. The method of claim 14, wherein the non-naturally occurring satellite cells are derived from a dedifferentiated myoblast.

16. The method of claim 14, wherein the non-naturally occurring satellite cells are expandable in culture.

17. The method of claim 14, wherein the non-naturally occurring satellite cells exhibit a response to a muscle injury.

18. The method of claim 14, wherein the non-naturally occurring satellite cells exhibit morphology that resembles the morphology of an endogenous satellite cell.

19. The method of claim 14, wherein the non-naturally occurring satellite cells further express at least one quiescence-related gene.

20. The method of claim 14, wherein the non-naturally occurring satellite cells further express at least one Notch signaling pathway gene.

21. The method of claim 14, wherein the non-naturally occurring satellite cells further express Myf5 and/or Pax7.

22. The method of claim 14, wherein the non-naturally occurring cells do not express MyoD.

23. The method of claim 14, wherein the non-naturally occurring satellite cells are encapsulated in a microcapsule.

24. A method for treatment of a muscle disorder in a subject in need thereof, the method comprising administering to the subject a pharmaceutical composition comprising therapeutically effective amount of an isolated population of non-naturally occurring satellite cells produced according to a method comprising:
 contacting a population of cells comprising myoblasts in spin culture with at least one medium for a time sufficient to induce the dedifferentiation of at least one myoblast in the spin culture into a non-naturally occurring satellite cell, wherein:
 the non-naturally occurring satellite cells produced have a gene expression profile that is different from the gene expression profile of an endogenous satellite cell;
 the non-naturally occurring satellite cells produced express two or more genes selected from the group consisting of: Nr2f1, Dmpl, Wisp2/Ccn5, Ecm1, Map, Igfbp5, Itgb5, Sdc2 and Bgn, wherein the expression of the two or more genes is upregulated by greater than 2-fold relative to expression by myoblasts and the two or more genes are not expressed in an endogenous satellite cell.

25. The method of claim 24, wherein the non-naturally occurring satellite cells are encapsulated in a microcapsule.

26. The method of claim 24, wherein the non-naturally occurring satellite cells are produced from a population of myoblasts obtained from the same subject to which the non-naturally occurring satellite cells are administered.

27. The method of claim 24, wherein the subject has, or has an increased risk of developing, a muscle degenerative disorder.

28. The method of claim 24, wherein the subject has, or has an increased risk of developing, muscle trauma.

29. The method of claim 24, wherein the subject has, or has an increased risk of developing, muscle atrophy.

30. A method for treatment of a muscle disorder in a subject in need thereof, the method comprising administering to the subject a pharmaceutical composition comprising therapeutically effective amount of an isolated population of non-naturally occurring satellite cells produced according to a method comprising:
 contacting a population of cells comprising myoblasts in spin culture with a first medium, wherein the first medium is a myoblast medium, to form an expanded myoblast population;
 contacting the expanded myoblast population with a second medium, wherein the second medium is a spin medium, to form at least one skeletal muscle organoid comprising differentiated and proliferative cells; and
 contacting the at least one skeletal muscle organoid in spin culture with a third medium, wherein the third medium is a differentiation medium, for a time sufficient to induce the dedifferentiation of at least one proliferative cell of the skeletal muscle organoid into a non-naturally occurring satellite cell,
 wherein the non-naturally occurring satellite cells produced express two or more genes selected from the group consisting of Nr2f1, Dmpl, Wisp2, Ecm1, and Mgp, and
 wherein the expression of the two or more genes is upregulated by greater than 2-fold relative to expression by myoblasts and the two or more genes are not expressed in an endogenous satellite cell.

* * * * *